(12) United States Patent
Auger et al.

(10) Patent No.: US 9,267,946 B2
(45) Date of Patent: *Feb. 23, 2016

(54) BIOMARKERS, METHODS AND KITS FOR THE DIAGNOSIS OF RHEUMATOID ARTHRITIS

(75) Inventors: Isabelle Auger, Marseilles (FR); Jean Roudier, Marseilles (FR)

(73) Assignees: INSERM (Institut National de la Sante et de la Rec, Paris (FR); UNIVERSITE DE LA MEDITERRANEE—AIX MARSEILLE 11, Marseille (FR)

( * ) Notice: Subject to any disclaimer, the term of this patent is extended or adjusted under 35 U.S.C. 154(b) by 639 days.

This patent is subject to a terminal disclaimer.

(21) Appl. No.: 13/259,645

(22) PCT Filed: Mar. 29, 2010

(86) PCT No.: PCT/EP2010/054087
§ 371 (c)(1),
(2), (4) Date: Dec. 12, 2011

(87) PCT Pub. No.: WO2010/115745
PCT Pub. Date: Oct. 14, 2010

(65) Prior Publication Data
US 2012/0083423 A1 Apr. 5, 2012

(30) Foreign Application Priority Data

Mar. 30, 2009 (EP) ..................... 09305266
Nov. 6, 2009 (EP) ..................... 09306063

(51) Int. Cl.
*A61K 39/12* (2006.01)
*C07K 4/00* (2006.01)
*A61K 38/04* (2006.01)
*A61K 38/16* (2006.01)
*G01N 33/532* (2006.01)
*G01N 33/564* (2006.01)
*C07K 14/47* (2006.01)
*C07K 14/81* (2006.01)
*C07K 14/82* (2006.01)
*C12N 9/12* (2006.01)
*C12N 9/78* (2006.01)
*G01N 33/68* (2006.01)

(52) U.S. Cl.
CPC .......... *G01N 33/564* (2013.01); *C07K 14/4713* (2013.01); *C07K 14/8139* (2013.01); *C07K 14/82* (2013.01); *C12N 9/1205* (2013.01); *C12N 9/78* (2013.01); *G01N 33/6854* (2013.01); *G01N 2800/102* (2013.01); *G01N 2800/60* (2013.01)

(58) Field of Classification Search
CPC ....................... G01N 33/564; G01N 2800/102
USPC ............................... 424/140.1; 436/506, 509
See application file for complete search history.

(56) References Cited

U.S. PATENT DOCUMENTS 4,208,479 A * 6/1980 Zuk et al. ................... 435/7.9
5,705,400 A * 1/1998 Furmaniak-Wehr .......... 436/506

FOREIGN PATENT DOCUMENTS

JP    2003 254966    9/2003
WO    2004/020595    3/2004

OTHER PUBLICATIONS (Colman et al., Res Immunol. Jan. 1994;145(1):33-6).*
ProtoArray Manual (2006, retrieved from URL https://abrc.osu.edu/sites/abrc.osu.edu/files/protoarray_humanPPI_v4_man.pdf ).*
Auger et al., "New autoantigens in rheumatoid arthritis (RA): screening 8268 protein arrays with sera from patients with RA," Ann. Rheum. Dis., 68(4):591-594 (2008) XP008111752.
Harris et al., "Association of autoimmunity to peptidyl arginine deiminase type 4 with genotype and disease severity in rheumatoid arthritis," Arthritis Rheum., 58(7):1958-1967 (2008) XP002545323.
International Search Report in PCT/EP2010/054087, dated Nov. 4, 2010.

* cited by examiner

*Primary Examiner* — Shafiqul Haq
*Assistant Examiner* — Carmencita M Belei
(74) *Attorney, Agent, or Firm* — McAndrews, Held & Malloy, Ltd.; Nabeela Rasheed; Christopher Singer

(57) ABSTRACT

The present invention relates to peptides biomarkers that are specifically recognized by autoantibodies present in the sera of patients with Rheumatoid Arthritis (RA). More specifically, the invention provides epitopes of PAD4, of BRAF, and of calpastatin as well as methods and kits for using these sequences for the diagnosis of RA, in particular for the diagnosis of RA in CCP-negative subjects.

5 Claims, 10 Drawing Sheets

A

B

C

|  |  | BRAF peptides | | |
|---|---|---|---|---|
| RA | CCP | P10 | P16 | P25 |
| RA1 | neg |  |  |  |
| RA2 | neg | ▓ |  | ▓ |
| RA3 | neg |  |  |  |
| RA4 | neg | ▓ |  |  |
| RA5 | neg | ▓ |  |  |
| RA6 | neg |  |  |  |
| RA7 | neg | ▓ |  |  |
| RA8 | neg |  |  |  |
| RA9 | neg | ▓ |  | ▓ |
| RA10 | neg |  |  |  |
| RA11 | neg |  |  |  |
| RA12 | neg |  |  |  |
| RA13 | neg | ▓ |  |  |
| RA14 | neg | ▓ |  | ▓ |
| RA15 | neg | ▓ |  | ▓ |
| RA16 | neg |  |  |  |
| RA17 | neg | ▓ | ▓ | ▓ |
| RA18 | neg |  |  |  |
| RA19 | neg |  |  |  |
| RA20 | neg |  |  | ▓ |
| RA21 | neg |  |  |  |
| RA22 | neg | ▓ |  |  |
| RA23 | neg |  |  |  |
| RA24 | neg | ▓ |  |  |
| RA25 | neg |  |  | ▓ |
| RA26 | neg |  |  |  |
| RA27 | neg |  |  |  |
| RA28 | neg | ▓ |  |  |
| RA29 | neg | ▓ |  | ▓ |

Figure 7

SEQUENCE LISTING

<160> NUMBER OF SEQ ID NOS: 12

<210> SEQ ID NO 1
<211> LENGTH: 663
<212> TYPE: PRT
<213> ORGANISM: Homo sapiens

<400> SEQUENCE: 1

```
Met Ala Gln Gly Thr Leu Ile Arg Val Thr Pro Glu Gln Pro Thr His
1               5                   10                  15

Ala Val Cys Val Leu Gly Thr Leu Thr Gln Leu Asp Ile Cys Ser Ser
            20                  25                  30

Ala Pro Glu Asp Cys Thr Ser Phe Ser Ile Asn Ala Ser Pro Gly Val
        35                  40                  45

Val Val Asp Ile Ala His Ser Pro Pro Ala Lys Lys Lys Ser Thr Gly
    50                  55                  60

Ser Ser Thr Trp Pro Leu Asp Pro Gly Val Glu Val Thr Leu Thr Met
65                  70                  75                  80

Lys Ala Ala Ser Gly Ser Thr Gly Asp Gln Lys Val Gln Ile Ser Tyr
                85                  90                  95

Tyr Gly Pro Lys Thr Pro Pro Val Lys Ala Leu Leu Tyr Leu Thr Ala
            100                 105                 110

Val Glu Ile Ser Leu Cys Ala Asp Ile Thr Arg Thr Gly Lys Val Lys
        115                 120                 125

Pro Thr Arg Ala Val Lys Asp Gln Arg Thr Trp Thr Trp Gly Pro Cys
    130                 135                 140

Gly Gln Gly Ala Ile Leu Leu Val Asn Cys Asp Arg Asp Asn Leu Glu
145                 150                 155                 160

Ser Ser Ala Met Asp Cys Glu Asp Asp Glu Val Leu Asp Ser Glu Asp
                165                 170                 175

Leu Gln Asp Met Ser Leu Met Thr Leu Ser Thr Lys Thr Pro Lys Asp
            180                 185                 190

Phe Phe Thr Asn His Thr Leu Val Leu His Val Ala Arg Ser Glu Met
        195                 200                 205

Asp Lys Val Arg Val Phe Gln Ala Thr Arg Gly Lys Leu Ser Ser Lys
    210                 215                 220

Cys Ser Val Val Leu Gly Pro Lys Trp Pro Ser His Tyr Leu Met Val
225                 230                 235                 240

Pro Gly Gly Lys His Asn Met Asp Phe Tyr Val Glu Ala Leu Ala Phe
                245                 250                 255

Pro Asp Thr Asp Phe Pro Gly Leu Ile Thr Leu Thr Ile Ser Leu Leu
            260                 265                 270

Asp Thr Ser Asn Leu Glu Leu Pro Glu Ala Val Val Phe Gln Asp Ser
        275                 280                 285

Val Val Phe Arg Val Ala Pro Trp Ile Met Thr Pro Asn Thr Gln Pro
    290                 295                 300

Pro Gln Glu Val Tyr Ala Cys Ser Ile Phe Glu Asn Glu Asp Phe Leu
305                 310                 315                 320

Lys Ser Val Thr Thr Leu Ala Met Lys Ala Lys Cys Lys Leu Thr Ile
                325                 330                 335

Cys Pro Glu Glu Glu Asn Met Asp Asp Gln Trp Met Gln Asp Glu Met
            340                 345                 350

Glu Ile Gly Tyr Ile Gln Ala Pro His Lys Thr Leu Pro Val Val Phe
        355                 360                 365
```

Asp Ser Pro Arg Asn Arg Gly Leu Lys Glu Phe Pro Ile Lys Arg Val
370             375                 380

Met Gly Pro Asp Phe Gly Tyr Val Thr Arg Gly Pro Gln Thr Gly Gly
385             390                 395                 400

Ile Ser Gly Leu Asp Ser Phe Gly Asn Leu Glu Val Ser Pro Pro Val
                405                 410                 415

Thr Val Arg Gly Lys Glu Tyr Pro Leu Gly Arg Ile Leu Phe Gly Asp
            420                 425                 430

Ser Cys Tyr Pro Ser Asn Asp Ser Arg Gln Met His Gln Ala Leu Gln
                435                 440                 445

Asp Phe Leu Ser Ala Gln Gln Val Gln Ala Pro Val Lys Leu Tyr Ser
450                 455                 460

Asp Trp Leu Ser Val Gly His Val Asp Glu Phe Leu Ser Phe Val Pro
465                 470                 475                 480

Ala Pro Asp Arg Lys Gly Phe Arg Leu Leu Leu Ala Ser Pro Arg Ser
                485                 490                 495

Cys Tyr Lys Leu Phe Gln Glu Gln Gln Asn Glu Gly His Gly Glu Ala
                500                 505                 510

Leu Leu Phe Glu Gly Ile Lys Lys Lys Gln Gln Lys Ile Lys Asn
                515                 520                 525

Ile Leu Ser Asn Lys Thr Leu Arg Glu His Asn Ser Phe Val Glu Arg
530                 535                 540

Cys Ile Asp Trp Asn Arg Glu Leu Leu Lys Arg Glu Leu Gly Leu Ala
545                 550                 555                 560

Glu Ser Asp Ile Ile Asp Ile Pro Gln Leu Phe Lys Leu Lys Glu Phe
                565                 570                 575

Ser Lys Ala Glu Ala Phe Phe Pro Asn Met Val Asn Met Leu Val Leu
                580                 585                 590

Gly Lys His Leu Gly Ile Pro Lys Pro Phe Gly Pro Val Ile Asn Gly
                595                 600                 605

Arg Cys Cys Leu Glu Glu Lys Val Cys Ser Leu Glu Pro Leu Gly
                610                 615                 620

Leu Gln Cys Thr Phe Ile Asn Asp Phe Phe Thr Tyr His Ile Arg His
625                 630                 635                 640

Gly Glu Val His Cys Gly Thr Asn Val Arg Arg Lys Pro Phe Ser Phe
                645                 650                 655

Lys Trp Trp Asn Met Val Pro
            660

<210> SEQ ID NO 2
<211> LENGTH: 20
<212> TYPE: PRT
<213> ORGANISM: Homo sapiens

<400> SEQUENCE: 2

Val Arg Val Phe Gln Ala Thr Arg Gly Lys Leu Ser Ser Lys Cys Ser
1               5                   10                  15

Val Val Leu Gly
            20

<210> SEQ ID NO 3
<211> LENGTH: 20
<212> TYPE: PRT
<213> ORGANISM: Homo sapiens

<400> SEQUENCE: 3

```
Pro Phe Gly Pro Val Ile Asn Gly Arg Cys Cys Leu Glu Glu Lys Val
1               5                   10                  15

Cys Ser Leu Leu
            20

<210> SEQ ID NO 4
<211> LENGTH: 20
<212> TYPE: PRT
<213> ORGANISM: Homo sapiens

<400> SEQUENCE: 4

Glu Pro Leu Gly Leu Gln Cys Thr Phe Ile Asn Asp Phe Phe Thr Tyr
1               5                   10                  15

His Ile Arg His
            20

<210> SEQ ID NO 5
<211> LENGTH: 40
<212> TYPE: PRT
<213> ORGANISM: Homo sapiens

<400> SEQUENCE: 5

Pro Phe Gly Pro Val Ile Asn Gly Arg Cys Cys Leu Glu Glu Lys Val
1               5                   10                  15

Cys Ser Leu Leu Glu Pro Leu Gly Leu Gln Cys Thr Phe Ile Asn Asp
            20                  25                  30

Phe Phe Thr Tyr His Ile Arg His
            35                  40

<210> SEQ ID NO 6
<211> LENGTH: 766
<212> TYPE: PRT
<213> ORGANISM: Homo sapiens

<400> SEQUENCE: 6

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
```

-continued

```
                180                 185                 190
Glu Cys Cys Ala Val Tyr Arg Ile Gln Asp Gly Glu Lys Lys Pro Ile
            195                 200                 205
Gly Trp Asp Thr Asp Ile Ser Trp Leu Thr Gly Glu Glu Leu His Val
            210                 215                 220
Glu Val Leu Glu Asn Val Pro Leu Thr Thr His Asn Phe Val Arg Lys
225                 230                 235                 240
Thr Phe Phe Thr Leu Ala Phe Cys Asp Phe Cys Arg Lys Leu Leu Phe
                245                 250                 255
Gln Gly Phe Arg Cys Gln Thr Cys Gly Tyr Lys Phe His Gln Arg Cys
                260                 265                 270
Ser Thr Glu Val Pro Leu Met Cys Val Asn Tyr Asp Gln Leu Asp Leu
                275                 280                 285
Leu Phe Val Ser Lys Phe Phe Glu His His Pro Ile Pro Gln Glu Glu
            290                 295                 300
Ala Ser Leu Ala Glu Thr Ala Leu Thr Ser Gly Ser Ser Pro Ser Ala
305                 310                 315                 320
Pro Ala Ser Asp Ser Ile Gly Pro Gln Ile Leu Thr Ser Pro Ser Pro
                325                 330                 335
Ser Lys Ser Ile Pro Ile Pro Gln Pro Phe Arg Pro Ala Asp Glu Asp
                340                 345                 350
His Arg Asn Gln Phe Gly Gln Arg Asp Arg Ser Ser Ser Ala Pro Asn
                355                 360                 365
Val His Ile Asn Thr Ile Glu Pro Val Asn Ile Asp Asp Leu Ile Arg
            370                 375                 380
Asp Gln Gly Phe Arg Gly Asp Gly Gly Ser Thr Thr Gly Leu Ser Ala
385                 390                 395                 400
Thr Pro Pro Ala Ser Leu Pro Gly Ser Leu Thr Asn Val Lys Ala Leu
                405                 410                 415
Gln Lys Ser Pro Gly Pro Gln Arg Glu Arg Lys Ser Ser Ser Ser Ser
                420                 425                 430
Glu Asp Arg Asn Arg Met Lys Thr Leu Gly Arg Arg Asp Ser Ser Asp
            435                 440                 445
Asp Trp Glu Ile Pro Asp Gly Gln Ile Thr Val Gly Gln Arg Ile Gly
            450                 455                 460
Ser Gly Ser Phe Gly Thr Val Tyr Lys Gly Lys Trp His Gly Asp Val
465                 470                 475                 480
Ala Val Lys Met Leu Asn Val Thr Ala Pro Thr Pro Gln Gln Leu Gln
                485                 490                 495
Ala Phe Lys Asn Glu Val Gly Val Leu Arg Lys Thr Arg His Val Asn
                500                 505                 510
Ile Leu Leu Phe Met Gly Tyr Ser Thr Lys Pro Gln Leu Ala Ile Val
            515                 520                 525
Thr Gln Trp Cys Glu Gly Ser Ser Leu Tyr His His Leu His Ile Ile
            530                 535                 540
Glu Thr Lys Phe Glu Met Ile Lys Leu Ile Asp Ile Ala Arg Gln Thr
545                 550                 555                 560
Ala Gln Gly Met Asp Tyr Leu His Ala Lys Ser Ile Ile His Arg Asp
                565                 570                 575
Leu Lys Ser Asn Asn Ile Phe Leu His Glu Asp Leu Thr Val Lys Ile
                580                 585                 590
Gly Asp Phe Gly Leu Ala Thr Val Lys Ser Arg Trp Ser Gly Ser His
                595                 600                 605
```

```
Gln Phe Glu Gln Leu Ser Gly Ser Ile Leu Trp Met Ala Pro Glu Val
        610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
            645                 650                 655

Ser Asn Ile Asn Asn Arg Asp Gln Ile Ile Phe Met Val Gly Arg Gly
        660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Arg Asp Glu Arg
        690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
            725                 730                 735

Gly Phe Gln Thr Glu Asp Phe Ser Leu Tyr Ala Cys Ala Ser Pro Lys
        740                 745                 750

Thr Pro Ile Gln Ala Gly Gly Tyr Gly Ala Phe Pro Val His
        755                 760                 765

<210> SEQ ID NO 7
<211> LENGTH: 20
<212> TYPE: PRT
<213> ORGANISM: Homo sapiens

<400> SEQUENCE: 7

Arg Lys Thr Arg His Val Asn Ile Leu Leu Phe Met Gly Tyr Ser Thr
1               5                   10                  15

Lys Pro Gln Leu
            20

<210> SEQ ID NO 8
<211> LENGTH: 20
<212> TYPE: PRT
<213> ORGANISM: Homo sapiens

<400> SEQUENCE: 8

Tyr Leu His Ala Lys Ser Ile Ile His Arg Asp Leu Lys Ser Asn Asn
1               5                   10                  15

Ile Phe Leu His
            20

<210> SEQ ID NO 9
<211> LENGTH: 20
<212> TYPE: PRT
<213> ORGANISM: Homo sapiens

<400> SEQUENCE: 9

Tyr Ser Asn Ile Asn Asn Arg Asp Gln Ile Ile Phe Met Val Gly Arg
1               5                   10                  15

Gly Tyr Leu Ser
            20

<210> SEQ ID NO 10
<211> LENGTH: 708
<212> TYPE: PRT
<213> ORGANISM: Homo sapiens
```

<400> SEQUENCE: 10

```
Met Asn Pro Thr Glu Thr Lys Ala Ile Pro Val Ser Gln Gln Met Glu
1               5                   10                  15

Gly Pro His Leu Pro Asn Lys Lys His Lys Lys Gln Ala Val Lys
            20                  25                  30

Thr Glu Pro Glu Lys Lys Ser Gln Ser Thr Lys Leu Ser Val Val His
            35                  40                  45

Glu Lys Lys Ser Gln Glu Gly Lys Pro Lys Glu His Thr Glu Pro Lys
50                  55                  60

Ser Leu Pro Lys Gln Ala Ser Asp Thr Gly Ser Asn Asp Ala His Asn
65                  70                  75                  80

Lys Lys Ala Val Ser Arg Ser Ala Glu Gln Gln Pro Ser Glu Lys Ser
                85                  90                  95

Thr Glu Pro Lys Thr Lys Pro Gln Asp Met Ile Ser Ala Gly Gly Glu
            100                 105                 110

Ser Val Ala Gly Ile Thr Ala Ile Ser Gly Lys Pro Gly Asp Lys Lys
            115                 120                 125

Lys Glu Lys Lys Ser Leu Thr Pro Ala Val Pro Val Glu Ser Lys Pro
130                 135                 140

Asp Lys Pro Ser Gly Lys Ser Gly Met Asp Ala Ala Leu Asp Asp Leu
145                 150                 155                 160

Ile Asp Thr Leu Gly Gly Pro Glu Glu Thr Glu Glu Glu Asn Thr Thr
                165                 170                 175

Tyr Thr Gly Pro Glu Val Ser Asp Pro Met Ser Ser Thr Tyr Ile Glu
            180                 185                 190

Glu Leu Gly Lys Arg Glu Val Thr Ile Pro Pro Lys Tyr Arg Glu Leu
            195                 200                 205

Leu Ala Lys Lys Glu Gly Ile Thr Gly Pro Pro Ala Asp Ser Ser Lys
            210                 215                 220

Pro Ile Gly Pro Asp Asp Ala Ile Asp Ala Leu Ser Ser Asp Phe Thr
225                 230                 235                 240

Cys Gly Ser Pro Thr Ala Ala Gly Lys Lys Thr Glu Lys Glu Glu Ser
                245                 250                 255

Thr Glu Val Leu Lys Ala Gln Ser Ala Gly Thr Val Arg Ser Ala Ala
                260                 265                 270

Pro Pro Gln Glu Lys Lys Arg Lys Val Glu Lys Asp Thr Met Ser Asp
            275                 280                 285

Gln Ala Leu Glu Ala Leu Ser Ala Ser Leu Gly Thr Arg Gln Ala Glu
            290                 295                 300

Pro Glu Leu Asp Leu Arg Ser Ile Lys Glu Val Asp Glu Ala Lys Ala
305                 310                 315                 320

Lys Glu Glu Lys Leu Glu Lys Cys Gly Glu Asp Asp Glu Thr Ile Pro
                325                 330                 335

Ser Glu Tyr Arg Leu Lys Pro Ala Thr Asp Lys Asp Gly Lys Pro Leu
            340                 345                 350

Leu Pro Glu Pro Glu Glu Lys Pro Lys Pro Arg Ser Glu Ser Glu Leu
            355                 360                 365

Ile Asp Glu Leu Ser Glu Asp Phe Asp Arg Ser Glu Cys Lys Glu Lys
            370                 375                 380

Pro Ser Lys Pro Thr Glu Lys Thr Glu Glu Ser Lys Ala Ala Ala Pro
385                 390                 395                 400

Ala Pro Val Ser Glu Ala Val Cys Arg Thr Ser Met Cys Ser Ile Gln
                405                 410                 415
```

```
Ser Ala Pro Pro Glu Pro Ala Thr Leu Lys Gly Thr Val Pro Asp Asp
            420                 425                 430

Ala Val Glu Ala Leu Ala Asp Ser Leu Gly Lys Lys Glu Ala Asp Pro
                435                 440                 445

Glu Asp Gly Lys Pro Val Met Asp Lys Val Lys Glu Lys Ala Lys Glu
    450                 455                 460

Glu Asp Arg Glu Lys Leu Gly Lys Glu Glu Thr Ile Pro Pro Asp
465                 470                 475                 480

Tyr Arg Leu Glu Val Lys Asp Lys Asp Gly Lys Pro Leu Leu Pro
                485                 490                 495

Lys Glu Ser Lys Glu Gln Leu Pro Pro Met Ser Glu Asp Phe Leu Leu
            500                 505                 510

Asp Ala Leu Ser Glu Asp Phe Ser Gly Pro Gln Asn Ala Ser Ser Leu
            515                 520                 525

Lys Phe Glu Asp Ala Lys Leu Ala Ala Ile Ser Glu Val Val Ser
    530                 535                 540

Gln Thr Pro Ala Ser Thr Thr Gln Ala Gly Ala Pro Pro Arg Asp Thr
545                 550                 555                 560

Ser Gln Ser Asp Lys Asp Leu Asp Asp Ala Leu Asp Lys Leu Ser Asp
                565                 570                 575

Ser Leu Gly Gln Arg Gln Pro Asp Pro Asp Glu Asn Lys Pro Met Glu
            580                 585                 590

Asp Lys Val Lys Glu Lys Ala Lys Ala Glu His Arg Asp Lys Leu Gly
                595                 600                 605

Glu Arg Asp Asp Thr Ile Pro Pro Glu Tyr Arg His Leu Leu Asp Asp
610                 615                 620

Asn Gly Gln Asp Lys Pro Val Lys Pro Thr Lys Lys Ser Glu Asp
625                 630                 635                 640

Ser Lys Lys Pro Ala Asp Asp Gln Asp Pro Ile Asp Ala Leu Ser Gly
                645                 650                 655

Asp Leu Asp Ser Cys Pro Ser Thr Thr Glu Thr Ser Gln Asn Thr Ala
            660                 665                 670

Lys Asp Lys Cys Lys Lys Ala Ala Ser Ser Ser Lys Ala Pro Lys Asn
    675                 680                 685

Gly Gly Lys Ala Lys Asp Ser Ala Lys Thr Thr Glu Glu Thr Ser Lys
    690                 695                 700

Pro Lys Asp Asp
705

<210> SEQ ID NO 11
<211> LENGTH: 15
<212> TYPE: PRT
<213> ORGANISM: Homo sapiens

<400> SEQUENCE: 11

Ile Gly Pro Asp Asp Ala Ile Asp Ala Leu Ser Ser Asp Phe Thr
1               5                   10                  15

<210> SEQ ID NO 12
<211> LENGTH: 15
<212> TYPE: PRT
<213> ORGANISM: Homo sapiens

<400> SEQUENCE: 12

Ala Val Cys Arg Thr Ser Met Cys Ser Ile Gln Ser Ala Pro Pro
1               5                   10                  15
```

BIOMARKERS, METHODS AND KITS FOR THE DIAGNOSIS OF RHEUMATOID ARTHRITIS

RELATED APPLICATION

The present application is filed pursuant to 35 U.S.C. 371 as a U.S. National Phase application of International Patent Application No. PCT/EP2010/054087, which was filed Mar. 29, 2010, claiming the benefit of priority to European Patent Application No. EP 09 305 266.1 filed on Mar. 30, 2009 and European Patent Application No. EP 09 306 063.0 filed on Nov. 6, 2009. The entire text of the aforementioned applications is incorporated herein by reference in its entirety.

BACKGROUND OF THE INVENTION

Rheumatoid arthritis (RA) is a chronic autoimmune disease affecting approximately 1% of the world's population. It is characterized by inflammation and cellular proliferation in the synovial lining of joints that can ultimately result in cartilage and bone destruction, joint deformity and loss of mobility. RA usually causes problems in several joints at the same time, often in a symmetric manner. Early RA tends to affect the smaller joints first, such as the joints in the wrists, hands, ankles and feet. As the disease progresses, joints of the shoulders, elbows, knees, hips, jaw and neck can also become involved. Unlike other arthritic conditions that only affect areas in or around joints, RA is a systemic disease which can cause inflammation in extra-articular tissues throughout the body including the skin, blood vessels, heart, lungs and muscles.

RA is associated with pain, deformity, decreased quality of life, and disability, which in turn affect patients' ability to lead a normal and productive life. Recent studies have shown that 5 years after the onset of the disease, approximately one third of patients with RA are no longer able to work, and within 10 years, half of the patients have substantial functional disability (A. Young et al., Rheumatology, 2007, 46: 350-357). Consequently, RA imposes an important economic burden on society. Considerable data also suggest that RA is associated with lowered life expectancy.

Although RA has been extensively studied, the etiology and pathogenesis of the disease remain incompletely understood. Factors that may increase the risk for RA include: sex of the individual (women are 2 to 3 times more likely than men to develop the disease); age (RA occurs more commonly between the ages of 40 and 60, although it can also strike children, teenagers and older adults); genetics (RA was found to be strongly associated with the inherited tissue type Major Histocompatibility Complex (MHC) antigen HLA-DR4—more specifically DRB1*0401 and DRB1*0404); and smoking (RA is about 4 times more common in smokers than non-smokers).

There is currently no reliable cure for RA. Treatment is essentially directed towards relieving pain, reducing inflammation, and stopping or slowing joint damage and bone destruction. The current therapeutic approach is to prescribe disease-modifying antirheumatic drugs (DMARDs) early in the condition, as RA patients treated early with such drugs have better outcomes, with greater preservation of function, less work disability, and smaller risk of premature death. Recent advances in the understanding of the pathophysiology of RA have led to the development of new DMARDs, called biological response modifiers. Biological DMARDs are designed to target and block the action of certain key cells or molecules, such as tumor necrosis factor-alpha (TNF-α), interleukin-1 (IL-1), T-cells, and B-cells, involved in the abnormal immune reaction associated with RA. In comparison with traditional DMARDs, the biological agents have a much more rapid onset of action and can offer better clinical response with effective long-term prevention of joint damage (J. K. D. de Vries-Bouwstra et al., Rheum. Dis. Clin. North Am., 2005, 31: 745-762).

Since irreversible joint destruction can be prevented by intervention at the early stages of the disease, early diagnosis of RA is important. However, definitive diagnosis of RA can be difficult. Immunologic tests that can be performed for the diagnosis of RA include, in particular, measurement of the levels of rheumatoid factor (RF), and anti-cyclic citrullinated peptide (anti-CCP) antibodies. Serological testing for RF is complicated by moderate sensitivity and specificity, and high rates of positivity in other chronic inflammatory and infectious diseases (T. Dorner et al., Curr. Opin. Rheumatol, 2004, 16: 246-253). Anti-CCP antibody testing is particularly useful in the diagnosis of RA, with high specificity, positivity early in the disease process, and ability to identify patients who are likely to have severe disease and irreversible damage. However, a negative result in anti-CCP antibody testing does not exclude RA.

Therefore, there is a great need for new biological markers of RA. In particular, biomarkers that would allow reliable diagnosis and monitoring of the early stages of the disease and permit early intervention to potentially prevent pain, joint destruction and long-term disability, are highly desirable.

SUMMARY OF THE INVENTION

The present invention generally relates to improved systems and strategies for the diagnosis of rheumatoid arthritis (RA). In particular, the invention relates to peptide biomarkers that specifically react with autoantibodies present in the sera of RA patients. More specifically, the present invention concerns amino acid sequences of human PAD4, BRAF and calpastatin, and methods for using such sequences in the diagnosis of RA, in particular in the diagnosis of RA in CCP-negative patients.

Thus, in one aspect, the present invention provides an in vitro method for diagnosing RA in a subject, said method comprising steps of: contacting a biological sample obtained from the subject with at least one biomarker for a time and under conditions allowing a biomarker-antibody complex to form; and detecting any biomarker-antibody complex formed.

In this method of diagnosis, the at least one biomarker is selected from the group consisting of:

PAD4-peptides having an amino acid sequence comprising or consisting of a sequence selected from the group consisting of SEQ ID NO: 2, SEQ ID NO: 3, SEQ ID NO: 4, SEQ ID NO: 5, analogues thereof, and fragments thereof, BRAF-peptides having an amino acid sequence comprising or consisting of a sequence selected from the group consisting of SEQ ID NO: 7, SEQ ID NO: 8, SEQ ID NO: 9, analogues thereof, and fragments thereof, calpastatin-peptides having an amino acid sequence comprising or consisting of a sequence selected from the group consisting of SEQ ID NO: 11, SEQ ID NO: 12, analogues thereof, and fragments thereof, and any combination thereof; and In certain embodiments, the at least one biomarker is selected from the group consisting of:

PAD4-peptides having an amino acid sequence consisting of a sequence selected from the group consisting of SEQ ID NO: 2, SEQ ID NO: 3, SEQ ID NO: 4, SEQ ID NO: 5, analogues thereof, and fragments thereof, BRAF-peptides having an amino acid sequence consisting of a sequence selected from the group consisting of SEQ ID NO: 7, SEQ ID NO: 8, SEQ ID NO: 9, analogues thereof, and fragments thereof, calpastatin-peptides having an amino acid sequence consisting of a sequence selected from the group consisting of SEQ ID NO: 11, SEQ ID NO: 12, analogues thereof, and fragments thereof, and any combination thereof.

In certain embodiments, a plurality of peptide biomarkers (i.e., two or more than two peptide biomarkers) is used in the method of diagnosis. In other words, the method of the invention may comprise steps of: contacting the biological sample with a plurality of biomarkers for a time and under conditions allowing biomarker-antibody complexes to form between one or more biomarkers and autoantibodies present in the biological sample; and detecting any biomarker-antibody complex formed.

In certain embodiments, the method of diagnosis is performed using eight peptide biomarkers including three PAD4-peptides, three BRAF-peptides and two calpastatin-peptides as described herein. In certain preferred embodiments, the three PAD4-peptides consist of SEQ ID NOs: 2-4, the three BRAF-peptides consist of SEQ ID NOs: 7-9, and the two calpastatin-peptides consist of SEQ ID NOs: 11-12.

In another aspect, the invention provides a method for detecting the presence of anti-PAD4 autoantibodies in a biological sample. The method comprises steps of: contacting the biological sample with at least one biomarker for a time and under conditions allowing a biomarker-antibody complex to form, wherein the at least one biomarker is a PAD4 peptide having an amino acid sequence comprising or consisting of a sequence selected from the group consisting of SEQ ID NO: 2, SEQ ID NO: 3, SEQ ID NO: 4, SEQ ID NO: 5, analogues thereof, fragments thereof, and any combination thereof; and detecting any biomarker-antibody complex formed. The detection of a biomarker-antibody complex is indicative of the presence of anti-PAD4 autoantibodies in the biological sample, and therefore of RA in the subject from whom the biological sample has been obtained.

The invention also provides a method for detecting the presence of anti-BRAF autoantibodies in a biological sample. The method comprises steps of: contacting the biological sample with at least one biomarker for a time and under conditions allowing a biomarker-antibody complex to form, wherein the at least one biomarker is a BRAF-peptide having an amino acid sequence comprising or consisting of a sequence selected from the group consisting of SEQ ID NO: 7, SEQ ID NO: 8, SEQ ID NO: 9, analogues thereof, fragments thereof, and any combination thereof; and detecting any biomarker-antibody complex formed. The detection of a biomarker-antibody complex is indicative of the presence of anti-BRAF autoantibodies in the biological sample, and therefore of RA in the subject from whom the biological sample has been obtained.

A biological sample, obtained from the subject to be tested and suitable for use in a method of the present invention, may be selected from the group consisting of whole blood, serum, plasma, urine, and synovial fluid. In certain preferred embodiments, the biological sample is a serologic sample, e.g., a blood sample. A blood sample, obtained from the subject and suitable for use in a method of diagnosis of the present invention, may be selected from the group consisting of whole blood, plasma, and serum.

In certain embodiments, the subject to be tested is CCP-negative or the biological sample to be tested is obtained from a CCP-negative subject.

In the methods of diagnosis provided herein, the step of detecting any biomarker-antibody complex formed between a peptide biomarker and an autoantibody present in the biological sample may be performed by any suitable method. In certain embodiments, the detection is by immunoassay.

In certain embodiments, the peptide biomarker or biomarkers used in the diagnosis method is/are immobilized on a solid carrier or support.

In certain embodiments, the methods of diagnosis may further comprise measuring, in a biological sample obtained from the subject, the concentration of at least one marker selected from the group consisting of C-reactive protein, serum amyloid A, interleukin 6, S100 proteins, osteopontin, rheumatoid factor, matrix metalloprotease 1, matrix metalloprotease 3, hyaluronic acid, sCD14, angiogenesis markers, and products of bone, cartilage and synovium metabolism.

In another aspect, the present invention provides kits for the in vitro diagnosis of RA in a subject. These kits comprise: at least one peptide biomarker of the invention and at least one reagent for detecting a biomarker-antibody complex formed between the peptide biomarker and an autoantibody present in the biological sample to be tested. In the kits, the at least one peptide biomarker may be immobilized on a solid carrier or support, or alternatively, reagents may be included in the kit that can be used to immobilize the peptide biomarker on a solid carrier or support. The kits may further comprise instructions for carrying out a method of diagnosis according to the present invention. In certain embodiments, the kit comprises at least eight biomarkers including three PAD4-peptides, three BRAF-peptides and two calpastatin-peptides as described herein. In certain preferred embodiments, the three PAD4-peptides consist of SEQ ID NOs: 2-4, the three BRAF-peptides consist of SEQ ID NOs: 7-9, and the two calpastatin-peptides consist of SEQ ID NOs: 11-12.

In yet another aspect, the present invention provides arrays for the diagnosis of RA in a subject. An array according to the invention comprises, attached to its surface, at least one peptide biomarker of the invention. In particular, the invention provides an array for the diagnosis of RA in CCP-negative subjects, the array comprising, attached to its surface, at least eight peptide biomarkers including three PAD4-peptides, three BRAF-peptides and two calpastatin-peptides described herein. In certain preferred embodiments, the three PAD4-pepides consist of SEQ ID NOs: 2-4, the three BRAF-peptides consist of SEQ ID NOs: 7-9, and the two calpastatin-peptides consist of SEQ ID NOs: 11-12. In certain embodiments, an inventive array further comprises, attached to its surface, at least one additional RA biomarker for detecting the presence of RA-specific autoantibodies, such as anti-nuclear antibodies and anti-CCP antibodies.

In still another aspect, the present invention provides peptide biomarkers of rheumatoid arthritis, preferably comprising less than 50 amino acid residues. In particular, the invention provides peptide biomarkers of less than 50 amino acid residues that are recognized by anti-PAD4 autoantibodies and which have an amino acid sequence comprising or consisting of a sequence selected from the group consisting of SEQ ID NO: 2, SEQ ID NO: 3, SEQ ID NO: 4, SEQ ID NO: 5, analogues thereof, and fragments thereof. The invention further provides peptide biomarkers of less than 50 amino acid residues that are recognized by anti-BRAF autoantibodies and which have an amino acid sequence comprising or consisting of a sequence selected from the group consisting of SEQ ID NO: 7, SEQ ID NO: 8, SEQ ID NO: 9, analogues thereof, and fragments thereof. The invention also provides peptide biomarkers of less than 50 amino acid residues that are recognized by anti-calpastatin autoantibodies and which have an amino acid sequence comprising or consisting of a sequence selected from the group consisting of SEQ ID NO: 11, SEQ ID NO: 12, analogues thereof, and fragments thereof, and wherein the biomarker is recognized by an anti-calpastatin autoantibody.

These and other objects, advantages and features of the present invention will become apparent to those of ordinary skill in the art having read the following detailed description of the preferred embodiment.

BRIEF DESCRIPTION OF THE DRAWING

FIG. 7 is a table showing that BRAF-peptides (P10, P16 and P25) identify RA in 50% of CCP-negative patients. Grey indicates a positive peptide (i.e., a BRAF peptide that undergoes binding to autoantibodies to BRAF present in the sera of CCP-negative patients). The binding was determined by ELISA as described in Example II.

DEFINITIONS

Figure 1:
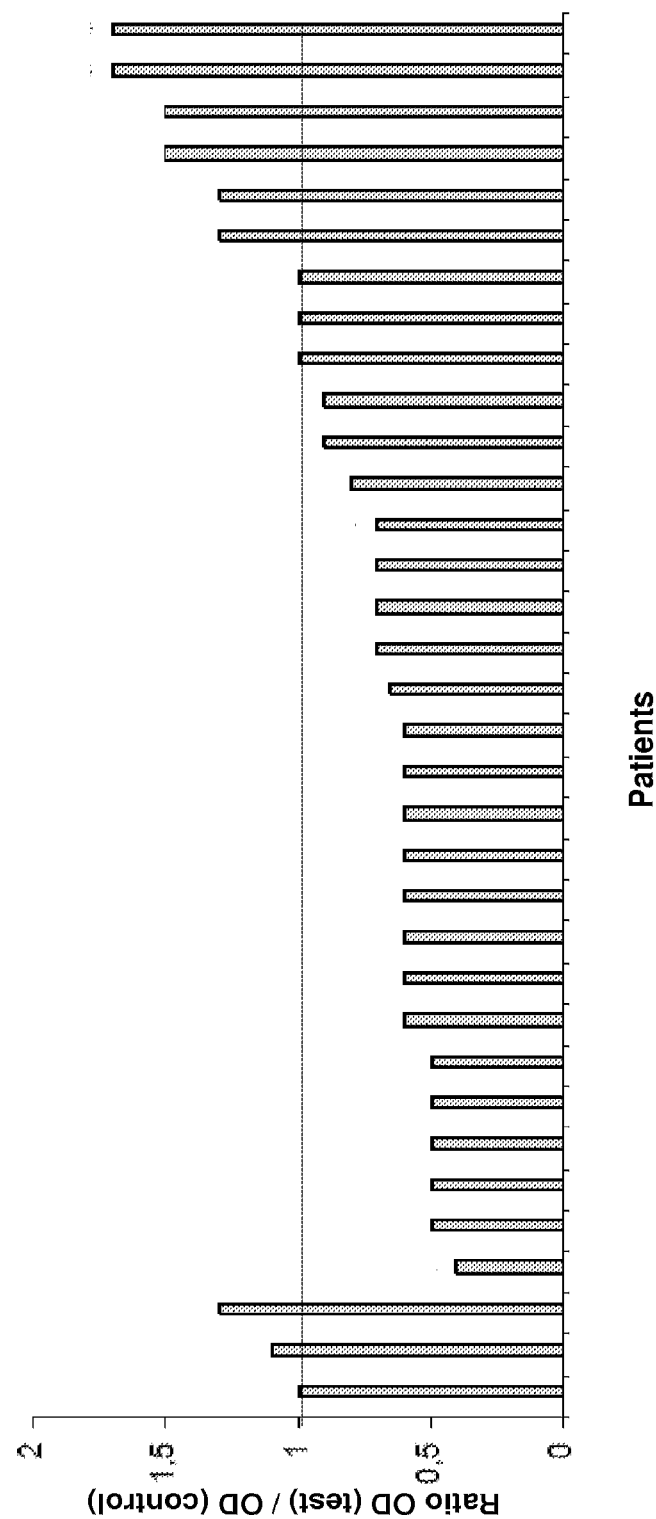
FIG. 1 is a graph showing that autoantibodies to PAD4 present in the serum of RA patients inhibit the citrullination of fibrinogen. The test was performed as described in the Examples section. A ratio of OD (test)/OD (control)>1 indicates an activation of the citrullination of fibrinogen by PAD4, while a ratio<1 indicates an inhibition of the citrullination of fibrinogen by PAD4.

Throughout the specification, several terms are employed that are defined in the following paragraphs.

As used herein, the term "subject" refers to a human or another mammal (e.g., primate, dog, cat, goat, horse, pig, mouse, rat, rabbit, and the like), that can be afflicted with RA, but may or may not have the disease. In many embodiments of the present invention, the subject is a human being. In such embodiments, the subject is often referred to as an "individual". The term "individual" does not denote a particular age, and thus encompasses children, teenagers, and adults.

The term "subject suspected of having RA" refers to a subject that presents one or more symptoms indicative of RA (e.g., pain, stiffness or swelling of joints), or that is screened for RA (e.g., during a physical examination). Alternatively or additionally, a subject suspected of having RA may have one or more risk factors (e.g., age, sex, family history, smoking, etc). The term encompasses subjects that have not been tested for RA as well as subjects that have received an initial diagnosis.

The term "biological sample" is used herein in its broadest sense. A biological sample is generally obtained from a subject. A sample may be of any biological tissue or fluid with which biomarkers of the present invention may be assayed. Frequently, a sample will be a "clinical sample", i.e., a sample derived from a patient. Such samples include, but are not limited to, bodily fluids which may or may not contain cells, e.g., blood (e.g., whole blood, serum or plasma), urine, synovial fluid, saliva, tissue or fine needle biopsy samples, and archival samples with known diagnosis, treatment and/or outcome history. Biological samples may also include sections of tissues such as frozen sections taken for histological purposes. The term "biological sample" also encompasses any material derived by processing a biological sample. Derived materials include, but are not limited to, cells (or their progeny) isolated from the sample, or proteins extracted from the sample. Processing of a biological sample may involve one or more of: filtration, distillation, extraction, concentration, inactivation of interfering components, addition of reagents, and the like. In certain preferred embodiments of the invention, the biological sample is a serologic sample and is (or is derived from) whole blood, serum or plasma obtained from a subject.

The terms "normal" and "healthy" are used herein interchangeably. They refer to a subject that has not shown any RA symptoms, and that has not been diagnosed with RA or with cartilage or bone injury. Preferably, a normal subject is not on medication affecting RA and has not been diagnosed with any other disease (in particular an autoimmune inflammatory disease). In certain embodiments, normal subjects may have similar sex, age, and/or body mass index as compared with the subject from which the biological sample to be tested was obtained. The term "normal" is also used herein to qualify a sample obtained from a healthy subject.

In the context of the present invention, the term "control", when used to characterize a subject, refers to a subject that is healthy or to a patient who has been diagnosed with a specific disease other than RA. The term "control sample" refers to one, or more than one, sample that has been obtained from a healthy subject or from a patient diagnosed with a disease other than RA.

The term "autoantibody", as used herein, has its art understood meaning, and refers to an antibody that is produced by the immune system of a subject and that is directed against one or more of the subject's own proteins. Autoantibodies may attack the body's own cells, tissues, and/or organs, causing inflammation and damage.

As used herein, the term "autoantigen" refers to an endogenous antigen, or an active fragment thereof, that stimulates the production of autoantibodies in a subject's body, as in autoimmune reactions. The term also encompasses any substances that can form an antigen-antibody complex with autoantibodies present in a subject or in a biological sample obtained from a subject.

The terms "biomarker" and "marker" are used herein interchangeably. They refer to a substance that is a distinctive indicator of a biological process, biological event, and/or pathologic condition. In the context of the present invention, the term "biomarker of RA" encompasses BRAF-peptides, PAD4-peptides and calpastatin-peptides provided herein which are specifically recognized by anti-PAD4 autoantibodies present in a biological sample (e.g., blood sample) of a RA patient. In certain preferred embodiments, the biomarkers of the invention are peptides of less than 50 amino acids.

As used herein, the term "indicative of RA", when applied to a process or event, refers to a process or event which is diagnostic of RA, such that the process or event is found significantly more often in subjects with RA than in healthy subjects and/or in subjects suffering from a disease other than RA.

The terms "protein", "polypeptide", and "peptide" are used herein interchangeably, and refer to amino acid sequences of a variety of lengths, either in their neutral (uncharged) forms or as salts, and either unmodified or modified by glycosylation, side chain oxidation, or phosphorylation. In certain embodiments, the amino acid sequence is a full-length native protein. In other embodiments, the amino acid sequence is a smaller fragment of the full-length protein. In still other embodiments, the amino acid sequence is modified by additional substituents attached to the amino acid side chains, such as glycosyl units, lipids, or inorganic ions such as phosphates, as well as modifications relating to chemical conversion of the chains such as oxidation of sulfhydryl groups. Thus, the term "protein" (or its equivalent terms) is intended to include the amino acid sequence of the full-length native protein, or a fragment thereof, subject to those modifications that do not significantly change its specific properties. In particular, the term "protein" encompasses protein isoforms, i.e., variants that are encoded by the same gene, but that differ in their pI or MW, or both. Such isoforms can differ in their amino acid sequence (e.g., as a result of alternative splicing or limited proteolysis), or in the alternative, may arise from differential post-translational modification (e.g., glycosylation, acylation, phosphorylation).

The term "analog", when used herein in reference to a protein or polypeptide, refers to a peptide that possesses a similar or identical function as the protein or polypeptide but need not necessarily comprise an amino acid sequence that is similar or identical to the amino acid sequence of the protein or polypeptide or a structure that is similar or identical to that of the protein or polypeptide. Preferably, in the context of the present invention, an analog has an amino acid sequence that is at least 30%, more preferably, at least about: 35%, 40%, 45%, 50%, 55%, 60%, 65%, 70%, 75%, 80%, 85%, 90%, 95% or 99%, identical to the amino acid sequence of the protein or polypeptide. In certain preferred embodiments, an analog of a peptide biomarker of the invention has an amino acid sequence that is at least 80% identical or at least 85% identical to the amino acid sequence of the peptide biomarker.

The term "fragment", when used herein in reference to a protein or polypeptide, refers to a peptide comprising an amino acid sequence of at least 5 amino acid residues (preferably, of at least about: 10, 15, 20, 25, 30, 40, 50, 60, 70, 80, 90, 100, 125, 150, 175, 200, or 250 amino acid residues) of the amino acid sequence of a protein or polypeptide. The fragment of a protein or polypeptide may or may not possess a functional activity of the protein or polypeptide. In certain preferred embodiments of the present invention, a fragment of a peptide biomarker of the invention comprises an amino acid sequence of at least 10 consecutive amino acid residues of the amino acid sequence of the peptide biomarker.

The term "homologous" (or "homology"), as used herein, is synonymous with the term "identity" and refers to the sequence similarity between two polypeptide molecules or between two nucleic acid molecule. When a position in both compared sequences is occupied by the same base or same amino acid residue, then the respective molecules are homologous at that position. The percentage of homology between two sequences corresponds to the number of matching or homologous positions shared by the two sequences divided by the number of positions compared and multiplied by 100. Generally, a comparison is made when two sequences are aligned to give maximum homology. Homologous amino acid sequences share identical or similar amino acid sequences. Similar residues are conservative substitutions for, or "allowed point mutations" of, corresponding amino acid residues in a reference sequence. "Conservative substitutions" of a residue in a reference sequence are substitutions that are physically or functionally similar to the corresponding reference residue, e.g., that have a similar size, shape, electric charge, chemical properties, including the ability to form covalent or hydrogen bonds, or the like. Particularly preferred conservative substitutions are those fulfilling the criteria defined for an "accepted point mutation" by Dayhoff et al. ("Atlas of Protein Sequence and Structure", 1978, Nat. Biomed. Res. Foundation, Washington, D.C., Suppl. 3, 22: 354-352).

The terms "labeled", "labeled with a detectable agent" and "labeled with a detectable moiety" are used herein interchangeably. These terms are used to specify that an entity (e.g., a PAD4-peptide, a BRAF-peptide or a calpastatin-peptide) can be visualized, for example, following binding to another entity (e.g., an anti-PAD4 autoantibody, an anti-BRAF autoantibody or an anti-calpastatin-autoantibody). Preferably, a detectable agent or moiety is selected such that it generates a signal which can be measured and whose intensity is related to the amount of bound entity. In array-based methods, a detectable agent or moiety is also preferably selected such that it generates a localized signal, thereby allowing spatial resolution of the signal from each spot on the array. Methods for labeling proteins and polypeptides are well-known in the art. Labeled polypeptides can be prepared by incorporation of or conjugation to a label, that is directly or indirectly detectable by spectroscopic, photochemical, biochemical, immunochemical, electrical, optical, or chemical means, or any other suitable means Suitable detectable agents include, but are not limited to, various ligands, radionuclides, fluorescent dyes, chemiluminescent agents, microparticles, enzymes, colorimetric labels, magnetic labels, and haptens.

The terms "protein array" and "protein chip" are used herein interchangeably. They refer to a substrate surface on which different proteins or polypeptides have been immobilized, in an ordered manner, at discrete spots on the substrate. Protein arrays may be used to identify protein/protein interactions (e.g., antigen/antibody interactions), to identify the substrates of enzymes, or to identify the targets of biologically active small molecules. The term "microarray" more specifically refers to an array that is miniaturized so as to require microscopic examination for visual evaluation.

The term "treatment" is used herein to characterize a method that is aimed at (1) delaying or preventing the onset of a disease or condition (e.g., RA); (2) slowing down or stopping the progression, aggravating, or deteriorations of the symptoms of the condition; (3) bringing about ameliorations or the symptoms of the condition; and/or (4) curing the condition. A treatment may be administered prior to the onset of the disease, for a prophylactic or preventive action. It may also be administered after initiation of the disease, for a therapeutic action.

DETAILED DESCRIPTION OF CERTAIN PREFERRED EMBODIMENTS

As mentioned above, the present invention provides biomarkers that can be used for detecting the presence of RA-specific autoantibodies in biological samples obtained from patients. These biomarkers are PAD4-peptides corresponding to epitopes on human PAD4 and which specifically react with anti-PAD4 autoantibodies present in the serum of RA patients. Other biomarkers are BRAF-peptides that are epitopes on the autoantigen BRAF. Still other biomarkers are calpastatin-peptides. Preferably, the biomarkers are peptides of less than 50 amino acids. Also provided are methods for using these biomarkers for the diagnosis of RA.

I—Peptide Biomarkers

PAD4-Peptides

Critical antibodies in RA are directed at citrullin residues on different proteins such as Fibrin, Filaggrin, and Vimentin. Citrullin is generated by post-translational conversion of arginine residues. This process is catalyzed by a group of calcium-dependent peptidyl arginine deiminases, PADs. One of the PAD enzymes, PAD4 is widely believed to play a causative role in RA disease onset and progression because RA-associated mutations in the PAD4 gene have been identified in a variety of populations (A. Suzuki et al., Nat. Genet., 2003, 34(4): 395-402; T. Iwamoto et al., Rheumatology, 2006, 45: 804-807; S. M. Harney et al., Rheumatology, 2005, 44: 869-872; T; Cantaert et al., Ann. Rheum. Dis., 2005, 64: 1316-1320).

PAD4 is not only involved in the generation of citrullinated epitopes, it is in itself a target for RA-specific antibodies. Autoantibodies against PAD4 have already been described in RA patients (Y. Takizawa et al., Scand. J. Rheumatol., 2005, 3: 212-215; E. B. Roth et al., Clin. Exp. Rheumatol., 2006, 1: 12-18; E. H. Halvorsen et al., Ann. Rheumatol. Dis., 2008, 67: 414-417; J. Zhao et al., J. Rheumatol., 2008, 35: 969-974). In 2008, the present Applicants have identified autoantibodies against PAD4 in RA patients using protein array and ELISA analysis (I. Auger et al., Rheum. Dis., 2009, 68: 591-594; EP 08 305 167, each of which is incorporated by reference in its entirety). They observed that 29% of 116 patients were positive to PAD4 compared to none of 33 patients with spondylarthropathy (AS) and 3% of 60 healthy controls (p=0 by chi square test, 116 RA patients versus 93 controls).

As described in Example I below, the present Applicants have now identified epitopes on human PAD4 that are specifically recognized by the sera of RA patients. These epitopes were identified using 65 overlapping 20-mer peptides (see Table 1 of EP 09 305 266.1) encompassing the entire sequence of human PAD4 (GenBank Accession Number: NP_036519.1; locus NM_012387; SEQ ID NO: 1). These peptides were screened with the sera of 29 RA patients and 2 controls known to contain autoantibodies to PAD4. Among the 65 peptides, 18 were recognized by the sera tested. Four peptides (peptides 22, 28, 61 and 63) were preferentially recognized by the sera of RA patients and controls containing anti-PAD4 autoantibodies (see Table 2). To further confirm these results, the Applicants have tested the sera of 33 patients with spondylarthropathy (AS) and 33 healthy individuals by ELISA using peptides 22, 28, 61 and 63 as immunosorbents. Autoantibodies recognizing peptides 22, 61 and 63 were found in significantly higher percentage in the sera of RA patients than in controls (AS patients and healthy individuals). In contrast, autoantibodies recognizing peptide 28 were found in high percentage in the sera of RA patients as well as in the sera of controls (see FIG. 2).

Peptide 22 identified as described herein is located in the N terminal domain of PAD4 and has the following amino acid sequence:

SEQ ID NO: 2
VRVFQATRGKLSSKCSVVLG, which corresponds to amino acid residues 211 to 230 of human PAD4.

Peptide 61 identified as described herein is located in the C terminal domain of PAD4 and has the following amino acid sequence:

SEQ ID NO: 3
PFGPVINGRCCLEEKVCSLL, which corresponds to amino acid residues 601 to 620 of human PAD4.

Peptide 63 identified as described herein is located in the C terminal domain of PAD4 and has the following amino acid sequence:

SEQ ID NO: 4
EPLGLQCTFINDFFTYHIRH, which corresponds to amino acid residues 621 to 640 of human PAD4.

Accordingly, in one aspect, the present invention provides PAD4-peptides that are specifically recognized by anti-PAD4 autoantibodies present in the sera of RA patients. PAD4-peptides of the invention have an amino acid sequence, preferably of less than 50 amino acids, comprising or consisting of a sequence selected from the group consisting of SEQ ID NO: 2, SEQ ID NO: 3, SEQ ID NO: 4, SEQ ID NO: 5, analogues thereof, and homologues thereof. SEQ ID NOs: 2-4 are as described above. SEQ ID NO: 5 has the following amino acid sequence:

SEQ ID NO: 5
PFGPVINGRCCLEEKVCSLLEPLGLQCTFINDFFTYHIRH, which corresponds to amino acid residues 601 to 640 of human PAD4.

BRAF-Peptides

BRAF (also called B-raf) is a serine-threonine kinase protein of the RAF protein family. In humans, the BRAF gene encodes a BRAF protein of 766 amino acid residues (GenBank Accession Number: NP_004324.1), whose sequence is defined in SEQ ID NO. 6.

The present Applicants have previously shown that BRAF catalytic domain (residues 456 to 712 in SEQ ID NO: 6) is a target of autoantibodies of patients affected with RA and is a specific marker of RA (I. Auger et al., Rheum. Dis., 2009, 68: 591-594; EP 08 305 167). The Applicants have now identified (see Example II) three linear peptides on BRAF catalytic domain that are recognized almost uniquely by RA patients. These BRAF-peptides, P10, P16 and P25, have been shown to be recognized by the sera of CCP-negative patients. The combined used of P10, P16 and P25 identifies 50% of CCP-negative patients.

Peptide P10 identified as described herein has the following amino acid sequence:

SEQ ID NO: 7
RKTRHVNILLFMGYSTKPQL, which corresponds to amino acid residues 506 to 525 of human BRAF.

Peptide P16 identified as described herein has the following amino acid sequence:

SEQ ID NO: 8
YLHAKSIIHRDLKSNNIFLH, which corresponds to amino acid residues 566 to 585 of human BRAF.

Peptide P25 identified as described herein has the following amino acid sequence:

SEQ ID NO: 9
YSNINNRDQIIFMVGRGYLS, which corresponds to amino acid residues 656 to 675 of human BRAF.

Accordingly, in one aspect, the present invention provides BARF-peptides that are specifically recognized by anti-BRAF autoantibodies present in the sera of RA patients. BRAF-peptides of the invention have an amino acid sequence, preferably of less than 50 amino acids, comprising or consisting of a sequence selected from the group consisting of SEQ ID NO: 7, SEQ ID NO: 8, SEQ ID NO: 9, analogues thereof, and homologues thereof. SEQ ID NOs: 7-9 are as described above.

Calpastatin-Peptides

The present Applicants have observed that sera of patients afflicted with RA and homozygous for HLA-DRB1*0404 recognized a 100 kD synovial protein identified as calpastatin (Auger et al. Ann. Rheum. Dis., 2007, 66: 1588-1593). Calpastatin is an endogenous calpain (calcium dependent cysteine protease) inhibitor, present in most mammalian tissues. Calpastatin consists of an amino-terminal domain L and four repetitive calpain inhibitor domains—domains 1 to 4 (Menard et al., Immun. Today, 1996, 17: 545-547). The amino acid sequence of human calpastatin isoform A is provided in SEQ ID NO: 10 (GenPept accession number: NP_001035908).

The present Applicants have previously identified (see Example III) two linear peptides on calpastatin that are recognized by the sera of CCP-negative patients: P'16 and P'28, which are 15-mer peptides from locus NP_001035908.

Peptide P'16 identified as described herein has the following amino acid sequence:

SEQ ID NO: 11
IGPDDAIDALSSDFT, which corresponds to amino acid residues 226 to 240 of human calpastatin isoform A and is located in repetitive calpain inhibitor domain 1.

Peptide P'28 identified as described herein has the following amino acid sequence:

SEQ ID NO: 12
AVCRTSMCSIQSAPP, which corresponds to amino acid residues 406 to 420 of human calpastatin isoform A and is located in repetitive calpain inhibitor domain 2.

Accordingly, in one aspect, the present invention provides calpastatin-peptides that are specifically recognized by anti-calpastatin autoantibodies present in the sera of RA patients. Calpastatin-peptides of the invention have an amino acid sequence, preferably of less than 50 amino acids, comprising or consisting of a sequence selected from the group consisting of SEQ ID NO: 11, SEQ ID NO: 12, analogues thereof, and homologues thereof. SEQ ID NOs: 11-12 are as described above.

Preparation of the Peptide Biomarkers

The peptide biomarkers of the present invention may be prepared by any suitable method, including chemical synthesis and recombinant methods.

The peptides of the invention are generally sufficiently short that chemical synthesis, using standard methods is feasible. Solid-phase peptide synthesis, which was initially described by R. B. Merrifield (J. Am. Chem. Soc. 1963, 85: 2149-2154) is a quick and easy approach to synthesizing peptides and small peptidic molecules of known sequences. A compilation of such solid-phase techniques may be found, for example, in "Solid Phase Peptide Synthesis" (Methods in Enzymology, G. B. Fields (Ed.), 1997, Academic Press: San Diego, Calif., which is incorporated herein by reference in its entirety). Most of these synthetic procedures involve the sequential addition of one or more amino acid residues or suitably protected amino acid residues to a growing peptide chain. For example, the carboxy group of the first amino acid is attached to a solid support via a labile bond, and reacted with the second amino acid, whose amino group has been, beforehand, chemically protected to avoid self-condensation. After coupling, the amino group is deprotected, and the process is repeated with the following amino acid. Once the desired peptide is assembled, it is cleaved off from the solid support, precipitated, and the resulting free peptide may be analyzed and/or purified as desired. Solution methods, as described, for example, in "The Proteins" (Vol. II, 3$^{rd}$ Ed., H. Neurath et al. (Eds.), 1976, Academic Press: New York, N.Y., pp. 105-237) may also be used to synthesize the biomarkers of the invention.

In certain embodiments, a peptide biomarker of the invention is provided immobilized onto a solid carrier or support (e.g., a bead or array). Methods for immobilizing polypeptide molecules onto a solid surface are known in the art. A peptide may be immobilized by being either covalently or passively bound to the surface of a solid carrier or support. Examples of suitable carrier or support materials include, but are not limited to, agarose, cellulose, nitrocellulose, dextran, Sephadex, Sepharose, carboxymethyl cellulose, polyacrylamides, polystyrene, polyvinyl chloride, polypropylene, filter paper, magnetite, ion-exchange resin, glass, polyamine-methyl-vinyl-ether-maleic acid copolymer, amino acid copolymer, ethylene-maleic acid copolymer, nylon, silk, and the like. Immobilization of a peptide biomarker on the surface of a solid carrier or support may involve crosslinking, covalent binding or physical adsorption, using methods well known in the art. The solid carrier or support may be in the form of a bead, a particle, a microplate well, an array, a cuvette, a tube, a membrane, or any other shape suitable for conducting a diagnostic method according to the invention (e.g., using an immunoassay).

In particular, the invention provides an array or protein array for the diagnosis of RA, comprising, immobilized to its surface, at least one peptide biomarker of the invention. Preferably, the array comprises more than one peptide biomarker of the invention. The array may further comprise at least one additional biomarker of RA. Suitable biomarkers of RA include biomarkers allowing detection of the presence of antinuclear antibodies and/or CCP antibodies.

The present invention also provides a protein bead suspension array for the diagnosis of RA. This bead suspension array comprises a suspension of one or more identifiable distinct particles or beads, wherein each bead contains coding features relating to its size, color or fluorescence signature and wherein each bead is coated with a peptide biomarker of the present invention. Examples of bead suspension arrays include the xMAP® bead suspension array (Luminex Corporation).

II—Diagnosis Methods

As mentioned above, the peptide biomarkers disclosed herein is specifically recognized by the sera of RA patients, and in particular by the sera of CCP-negative RA patients.

Accordingly, the present invention provides methods for diagnosing RA in a subject. Such methods comprise contacting a biological sample obtained from the subject to be tested with at least one biomarker for a time and under conditions allowing a biomarker-antibody complex to form; and detecting any biomarker-antibody formed.

In certain embodiments, the at least one biomarker is a PAD4-peptide having an amino acid sequence, preferably of less than 50 amino acids, comprising or consisting of a sequence selected from the group consisting of SEQ ID NO: 2, SEQ ID NO: 3, SEQ ID NO: 4, SEQ ID NO: 5, analogues thereof and fragments thereof. In these methods, the detection of a biomarker-antibody complex is indicative of the presence of anti-PAD4 autoantibodies in the biological sample, and therefore is indicative of RA in the subject. More than one PAD4-peptide may be used in these methods.

In other embodiments, the at least one biomarker is a BRAF-peptide having an amino acid sequence, preferably of less than 50 amino acids, comprising or consisting of a sequence selected from the group consisting of SEQ ID NO: 7, SEQ ID NO: 8, SEQ ID NO: 9, analogues thereof and fragments thereof. In these methods, the detection of a biomarker-antibody complex is indicative of the presence of anti-BRAF autoantibodies in the biological sample, and therefore is indicative of RA in the subject. More than one BRAF-peptide may be used in these methods.

The present invention also provides methods for diagnosing RA in a subject. Such methods comprise contacting a biological sample obtained from the subject to be tested with at least two biomarkers for a time and under conditions allowing a biomarker-antibody complex to form; and detecting any biomarker-antibody formed. The at least two biomarkers may be selected from:

PAD4-peptides having an amino acid sequence, preferably of less than 50 amino acids, comprising or consisting of a sequence selected from the group consisting of SEQ ID NO: 2, SEQ ID NO: 3, SEQ ID NO: 4, SEQ ID NO: 5, analogues thereof and fragments thereof;

BRAF-peptides having an amino acid sequence, preferably of less than 50 amino acids, comprising or consisting of a sequence selected from the group consisting of SEQ ID NO: 7, SEQ ID NO: 8, SEQ ID NO: 9, analogues thereof and fragments thereof, Calpastatin-peptides having an amino acid sequence, preferably of less than 50 amino acids, comprising or consisting of a sequence selected from the group consisting of SEQ ID NO: 11, SEQ ID NO: 12, analogues thereof and fragments thereof; and any combination thereof In this method, the detection of a biomarker-antibody complex is indicative of RA in the subject.

In other embodiments, more than two peptide biomarkers are used, for example, 3, 4, 5, 6, 7 or 8 peptide biomarkers. In certain preferred embodiments, 8 peptide biomarkers are used, i.e., three PAD4-peptides, three BRAF-peptides and two calpastatin-peptides. In particularly preferred embodiments, the three PAD4-peptides consist of SEQ ID NOs: 2-4, the three BRAF-peptides consist of SEQ ID NOs: 7-9 and the two calpastatin-peptides consist of SEQ ID NOs: 11-12.

Biological Samples

The methods of diagnosis of the present invention may be applied to the study of any type of biological samples allowing one or more inventive biomarkers to be assayed. Examples of suitable biological samples include, but are not limited to, urine, whole blood, serum, plasma, saliva, and synovial fluid. Biological samples used in the practice of the invention may be fresh or frozen samples collected from a subject, or archival samples with known diagnosis, treatment and/or outcome history. Biological samples may be collected by any non-invasive means, such as, for example, by drawing blood from a subject, or using fine needle aspiration or needle biopsy. In certain embodiments, the biological sample is a serologic sample and is selected from the group consisting of whole blood, serum, plasma.

In preferred embodiments, the inventive methods are performed on the biological sample itself without, or with limited, processing of the sample.

However, alternatively, the inventive methods may be performed on a protein extract prepared from the biological sample. In this case, the protein extract preferably contains the total protein content. Methods of protein extraction are well known in the art (see, for example "*Protein Methods*", D. M. Bollag et al., $2^{nd}$ Ed., 1996, Wiley-Liss; "*Protein Purification Methods: A Practical Approach*", E. L. Harris and S. Angal (Eds.), 1989; "*Protein Purification Techniques: A Practical Approach*", S. Roe, $2^{nd}$ Ed., 2001, Oxford University Press; "*Principles and Reactions of Protein Extraction, Purification, and Characterization*", H. Ahmed, 2005, CRC Press: Boca Raton, Fla.). Various kits can be used to extract proteins from bodily fluids and tissues. Such kits are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). User Guides that describe in great detail the protocol to be followed are usually included in all these kits. Sensitivity, processing time and costs may be different from one kit to another. One of ordinary skill in the art can easily select the kit(s) most appropriate for a particular situation.

Detection of Biomarker-Antibody Complexes

The diagnostic methods of the present invention generally involve detection of a biomarker-antigen complex formed between the peptide biomarker and an autoantibody present in the biological sample tested. In the practice of the invention, detection of such a complex may be performed by any suitable method (see, for example, E. Harlow and A. Lane, "*Antibodies: A Laboratories Manual*", 1988, Cold Spring Harbor Laboratory: Cold Spring Harbor, N.Y.).

For example, detection of a biomarker-antibody complex may be performed using an immunoassay. A wide range of immunoassay techniques is available, including radioimmunoassay, enzyme immunoassays (EIA), enzyme-linked immunosorbent assays (ELISA), and immunofluorescence immunoprecipitation. Immunoassays are well known in the art. Methods for carrying out such assays as well as practical applications and procedures are summarized in textbooks. Examples of such textbooks include P. Tijssen, In: Practice and theory of enzyme immunoassays, eds. R. H. Burdon and v. P. H. Knippenberg, Elsevier, Amsterdam (1990), pp. 221-278 and various volumes of Methods in Enzymology, Eds. S. P. Colowick et al., Academic Press, dealing with immunological detection methods, especially volumes 70, 73, 74, 84, 92 and 121. Immunoassays may be competitive or non-competitive.

For example, any of a number of variations of the sandwich assay technique may be used to perform an immunoassay. Briefly, in a typical sandwich assay applied to the detection of, for example, anti-PAD4 autoantibodies according to the present invention, an unlabeled PAD4-peptide biomarker is immobilized on a solid surface (as described above) and the biological sample to be tested is brought into contact with the bound biomarker for a time and under conditions allowing formation of a biomarker-antibody complex. Following incubation, an antibody that is labeled with a detectable moiety and that specifically recognizes antibodies from the species tested (e.g., an anti-human IgG for human subjects) is added and incubated under conditions allowing the formation of a ternary complex between any biomarker-bound autoantibody and the labeled antibody. Any unbound material is washed away, and the presence of any anti-PAD4 autoantibody in the sample is determined by observation/detection of the signal directly or indirectly produced by the detectable moiety. Variations on this assay include an assay, in which both the biological sample and the labeled antibody are added simultaneously to the immobilized PAD4-peptide biomarker.

The second antibody (i.e., the antibody added in a sandwich assay as described above) may be labeled with any suitable detectable moiety, i.e., any entity which, by its chemical nature, provides an analytically identifiable signal allowing detection of the ternary complex, and consequently detection of the biomarker-antibody complex.

Detection may be either qualitative or quantitative. Methods for labeling biological molecules such as antibodies are well-known in the art (see, for example, "*Affinity Techniques. Enzyme Purification: Part B*", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

The most commonly used detectable moieties in immunoassays are enzymes and fluorophores. In the case of an enzyme immunoassay (EIA or ELISA), an enzyme such as horseradish perodixase, glucose oxidase, beta-galactosidase, alkaline phosphatase, and the like, is conjugated to the second antibody, generally by means of glutaraldehyde or periodate. The substrates to be used with the specific enzymes are generally chosen for the production of a detectable color change, upon hydrolysis of the corresponding enzyme. In the case of immunofluorescence, the second antibody is chemically coupled to a fluorescent moiety without alteration of its binding capacity. After binding of the fluorescently labeled antibody to the biomarker-antibody complex and removal of any unbound material, the fluorescent signal generated by the fluorescent moiety is detected, and optionally quantified. Alternatively, the second antibody may be labeled with a radioisotope, a chemiluminescent moiety, or a bioluminescent moiety.

RA Diagnosis

In the methods of the present invention, detection of a biomarker-antibody complex is indicative of the presence of anti-PAD4 autoantibodies, anti-BRAF autoantibodies or anti-Calpastatin-autoantibodies in the biological sample tested and is therefore indicative of RA in the subject from which the biological sample was obtained. Thus, the methods of the present invention may be used for the diagnosis of RA in patients. In particular, methods of the invention may be used for testing subjects suspected of having RA.

It will be appreciated by one skilled in the art that diagnosis of RA may be made solely on the results obtained by a method provided herein. Alternatively, a physician may also consider other clinical or pathological parameters used in existing methods to diagnose RA. Thus, results obtained using methods of the present invention may be compared to and/or combined with results from other tests, assays or procedures performed for the diagnosis of RA. Such comparison and/or combination may help provide a more refine diagnosis.

For example, RA diagnosis methods of the present invention may be used in combination with ARA criteria (i.e., the American College of Rheumatology 1987 revised criteria for the classification of RA described in F. C. Arnett et al., Arthritis Rheum., 1988, 31: 315-324). According to the ARA criteria, a patient is said to have RA if the patient exhibits at least 4 of the 7 following criteria: 1) morning stiffness for at least 1 hour; 2) arthritis of 3 or more joint areas; 3) arthritis of hand joints; 4) symmetrical arthritis; 5) rheumatoid nodules; 6) serum rheumatoid factor (RF); and 7) radiographic changes, wherein criteria 1-4 must be present for at least 6 months.

Alternatively or additionally, results from RA diagnosis methods of the present invention may be used in combination with results from one or more assays that employ other RA biomarkers. Thus, in certain embodiments, diagnosis of RA may be based on results from a method of the invention and on results from one or more additional assays that use a different RA biomarker. For example, a panel of RA biomarkers may be tested either individually or simultaneously, e.g., using a chip or a bead-based array technology.

Examples of suitable RA biomarkers include, but are not limited to, CCP, C-reactive protein, serum amyloid A, interleukin 6 (IL6), S100 proteins, ostopontin, rheumatoid factor, matrix metalloprotease 1 (MMP-1), matrix metalloprotease 3 (MMP-3), hyaluronic acid, sCD14, angiogenesis markers (such as the vascular endothelial growth factor or VEGF), and products of bone, cartilage or synovium metabolism (such as pyridinoline or its glycosylated form; deoxy-pyridinoline; cross-linked telopeptides; collagen neoepitopes; CS846; cartilage oligomeric matrix protein; cartilage intermediate layer protein; matrilins, chondromodulatins, osteocalcin, and the like).

In certain embodiments, the methods of the invention are used for the diagnosis of RA in CCP-negative patients. Indeed, as reported herein in the Examples section, the applicants have shown, in particular, that a method of the invention using the combination of eight peptide biomarkers (3 PAD4-peptides, 3 BRAF-peptides, and 2 calpastatin-peptides) allows the diagnosis of RA in more than 70% of CCP-negative subjects. The terms "CCP-negative patient" and "CCP-negative subject" are used herein interchangeably. They refer to a subject whose serum contains no antibodies (or at least no detectable antibodies) directed against citrullinated proteins.

III—Kits

In another aspect, the present invention provides kits comprising materials useful for carrying out diagnostic methods according to the present invention. The diagnosis procedures provided herein may be performed by diagnostics laboratories, experimental laboratories, or practitioners. The invention provides kits that can be used in these different settings.

Materials and reagents for detecting anti-PAD4 autoantibodies, anti-BRAF-autoantibodies and/or anti-calpastatin-autoantibodies in a biological sample and/or for diagnosing RA in a subject according to the present invention may be assembled together in a kit. Each kit of the invention comprises at least one inventive peptide biomarker preferably in an amount that is suitable for detection of autoantibodies in a biological sample.

Thus, in certain embodiments, an inventive kit comprises at least one PAD4-peptide having an amino acid sequence, preferably of less than 50 amino acids, comprising or consisting of a sequence selected from the group consisting of SEQ ID NO: 2, SEQ ID NO: 3, SEQ ID NO: 4, SEQ ID NO: 5, analogues thereof and fragments thereof.

In other embodiments, an inventive kit comprises at least one BRAF-peptide having an amino acid sequence, preferably of less than 50 amino acids, comprising or consisting of a sequence selected from the group consisting of SEQ ID NO: 7, SEQ ID NO: 8, SEQ ID NO: 9, analogues thereof and fragments thereof.

In yet other embodiments, an inventive kit comprises at least two biomarkers selected from the group consisting of:

PAD4-peptides having an amino acid sequence, preferably of less than 50 amino acids, comprising or consisting of a sequence selected from the group consisting of SEQ ID NO: 2, SEQ ID NO: 3, SEQ ID NO: 4, SEQ ID NO: 5, analogues thereof and fragments thereof;

BRAF-peptides having an amino acid sequence, preferably of less than 50 amino acids, comprising or consisting of a sequence selected from the group consisting of SEQ ID NO: 7, SEQ ID NO: 8, SEQ ID NO: 9, analogues thereof and fragments thereof, Calpastatin-peptides having an amino acid sequence, preferably of less than 50 amino acids, comprising or consisting of a sequence selected from the group consisting of SEQ ID NO: 11, SEQ ID NO: 12, analogues thereof and fragments thereof, and any combination thereof.

In certain preferred embodiments, the kit comprises at least eight biomarkers: three PAD4-peptides, 3 BRAF-peptides and 2 calpastatin-peptides, as described above. Preferably, the three PAD4-peptides consist of SEQ ID NOs: 2-4, the three BRAF-peptides consist of SEQ ID NOs: 7-9, and the two calpastatin-peptides consist of SEQ ID NOs: 11-12.

The peptide biomarker(s) included in a kit may or may not be immobilized on as substrate surface (e.g., beads, array, and the like). Thus, in certain embodiments, an inventive kit may include an array for diagnosing RA as provided herein. Alternatively, a substrate surface may be included in an inventive kit for immobilization of the peptide biomarkers.

An inventive kit generally also comprises at least one reagent for the detection of a biomarker-antibody complex formed between the peptide biomarker included in the kit and an autoantibody present in a biological sample. Such a reagent may be, for example, a labeled antibody that specifically recognizes antibodies from the species tested (e.g., an anti-human IgG for human subjects), as described above.

Depending on the procedure, the kit may further comprise one or more of: extraction buffer and/or reagents, blocking buffer and/or reagents, immunodetection buffer and/or reagents, labeling buffer and/or reagents, and detection means. Protocols for using these buffers and reagents for performing different steps of the procedure may be included in the kit.

The different reagents included in an inventive kit may be supplied in a solid (e.g., lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain embodiments, a kit comprises instructions for using its components for the diagnosis of RA in a subject according to a method of the invention. Instructions for using the kit according to methods of the invention may comprise instructions for processing the biological sample obtained from the subject and/or for performing the test, and/or instructions for interpreting the results. A kit may also contain a notice in the form prescribed by a governmental agency regulating the manufacture, use or sale of pharmaceuticals or biological products.

IV—Development of New Therapeutics for RA

The PAD4 and/or BRAF epitopes identified by the Applicants may constitute attractive targets for the identification of compounds or substances potentially useful for treating RA or preventing RA progression.

As already mentioned above, PAD4 is not only the target for RA-specific antibodies, it is also involved in the generation of citrullinated epitopes. The present Applicants have shown that anti-PAD4 autoantibodies inhibit citrullination of fibrinogen by PAD4 (see Examples section). The Applicants have also shown that anti-PAD4 autoantibodies specifically recognize 3 epitopes on PAD4, 2 of which (peptides 61 and 63) are localized within the domain of substrate binding of PAD4. Preventing the binding of anti-PAD4 autoantibodies to these PAD4 epitopes could reverse the inhibiting action of autoantibodies and restore PAD4 enzymatic activity.

BRAF is an interesting target for autoantibodies. BRAF is a serine-threonine kinase involved in the transduction of mitogenic signals from the cell membrane to the nucleus. BRAF regulates the mitogen-activated protein kinases (MAPKs) signalling cascade. MAPKs are involved in signalling via the B cell antigen receptor, T cell receptor, Toll-like receptor and IL-1, IL-17 and TNFα receptors. MAPKs also play a role in the production of pro-inflammatory cytokines (TNFα, IL-1, IL-6). To test whether autoantibodies to BRAF may influence BRAF activity as a kinase, the Applicants have developed a phosphorylation assay using BRAF, MEK1 (its major substrate) and autoantibodies to BRAF purified from the sera of RA patients; and found that 80% of anti-BRAF autoantibodies activate phosphorylation of MEK1 by BRAF in vitro. This result suggests that anti-BRAF autoantibodies could activate the MAP kinase pathway through BRAF, leading to proinflammatory cytokine production and joint inflammation. The Applicants have also shown that anti-BRAF autoantibodies specifically recognize 3 epitopes on BRAF (peptides P10, P16 and P25). Therefore, anti-BRAF antibodies may constitute a target for the control of inflammation in RA.

Thus, screens may be developed to identify compounds or substances that prevent the binding of anti-PAD4 autoantibodies to PAD4 epitopes, in particular peptide 61 and/or peptide 63. Similarly, screens may be developed to identify compounds or substances that prevent the binding of anti-BRAF autoantibodies to BRAF epitopes, in particular to peptides P10, P16 and/or P25.

Such screens may be carried out in any suitable biological system such as a biological fluid, a biological fluid, or isolated cells. Generally, screens are performed using cells that can be grown in standard tissue culture ware. Suitable cells include all appropriate normal and transformed cells derived from any recognized sources.

Preferably, cells are of mammalian (human or animal, such as rodent or simian) origin. More preferably, cells are of human origin. Mammalian cells may be of any organ or tissue origin (e.g., bone, cartilage, or synovial fluid) and of any cell types as long as the cells express PAD4 and/or PAD4. Cells to be used in the practice of the methods of the present invention may be primary cells, secondary cells, or immortalized cells (e.g., established cell lines). They may be prepared by techniques well known in the art (for example, cells may be isolated from bone, cartilage or synovial fluid) or purchased from immunological and microbiological commercial resources (for example, from the American Type Culture Collection, Manassas, Va.). Alternatively or additionally, cells may be genetically engineered to contain, for example, a gene of interest. An assay developed for primary drug screening (i.e., first round(s) of screening) is preferably performed using established cell lines, which are commercially available and usually relatively easy to grow, while an assay to be used later in the drug development process is preferably performed using primary and secondary cells, which are generally more difficult to obtain, maintain and/or grow than immortalized cells but which represent better experimental models for in vivo situation. Screening methods may be performed using cells contained in a plurality of wells of a multi-well assay plate.

As will be appreciated by one of ordinary skill in the art, any kind of compounds or agents can be screened. A candidate compound may be a synthetic or natural compound; it may be a single molecule or a mixture or complex of different molecules. Candidate compounds may be screened individually. Alternatively, compounds comprised in collections or libraries may be screened simultaneously.

Collections of natural compounds in the form of bacterial, fungal, plant and animal extracts are available from, for example, Pan Laboratories (Bothell, Wash.) or MycoSearch (Durham, N.C.). Synthetic compound libraries are commercially available from Comgenex (Princeton, N.J.), Brandon Associates (Merrimack, N.H.), Microsource (New Milford, Conn.), and Aldrich (Milwaukee, Wis.). Libraries of candidate compounds have also been developed by and are commercially available from large chemical companies, including, for example, Merck, Glaxo Welcome, Bristol-Meyers-Squibb, Novartis, Monsanto/Searle, and Pharmacia UpJohn. Additionally, natural collections, synthetically produced libraries and compounds are readily modified through conventional chemical, physical, and biochemical means. Chemical libraries are relatively easy to prepare by traditional automated synthesis, PCR, cloning or proprietary synthetic methods (see, for example, S. H. DeWitt et al., Proc. Natl. Acad. Sci. U.S.A. 1993, 90:6909-6913; R. N. Zuckermann et al., J. Med. Chem. 1994, 37: 2678-2685; Carell et al., Angew. Chem. Int. Ed. Engl. 1994, 33: 2059-2060; P. L. Myers, Curr. Opin. Biotechnol. 1997, 8: 701-707).

Using peptide 61 and/or peptide 63 of PAD4 or peptide P10, peptide P16 and/or peptide P25 of BRAF as a target(s), useful agents for the treatment of RA may be found in any of a large variety of classes of chemicals.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Some of the results presented below have been reported by the present Applicants in a scientific article (Auger et al., Ann. Rheum. Dis., 2009, 68: 591-594), which is incorporated herein by reference in its entirety.

Example I

PAD4-Peptides for RA Diagnosis

Patients and Methods
RA Patients and Controls

RA patients were selected from the Rheumatology Ward at the Hospital La Conception in Marseille, France. These patients fulfilled the 1987 American College of Rheumatology criteria for RA (F. C. Arnett et al., Arthritis Rheum., 1988, 31: 315-324). Patients with spondylarthropathy (AS) were from the Rheumatology Ward at the Hospital La Conception in Marseille. Volunteers from the laboratory staff and the Marseille Blood Transfusion Center staff served as normal controls. All participants gave informed consent.
Purification of Autoantibodies to PAD4

ELISA plates were coated with 1 µg of PAD4 per well overnight at 4° C., using recombinant PAD4 protein (Abnova Corporation, H0023569P01). Sera from 29 RA patients and from 2 controls containing autoantibodies to PAD4 were selected (I. Auger et al., Ann. Rheum. Dis., 2008 Oct. 28). The sera were diluted to 1:2 in PBS and incubated for 3 hours. After washing, autoantibodies to PAD4 were purified in PBS pH 2, neutralized in 1M Tris buffer, and quantified. The presence of anti-PAD4 autoantibodies was confirmed by dot blot.
In-House Citrullination Assay Human Fibrinogen (Sigma) at a final concentration of 10 mg/mL was incubated with 1 µg of PAD4 (Abonova Corporation) in working buffer (100 mM Tris HCl, 5 mM $CaCl_2$, 5 mM DTT, pH 7.5) in presence of 1 µg of purified autoantibodies to PAD4, for 4 hours at 55° C. For each patient, one positive control was included (incubation of fibrinogen with PAD4 in working buffer in the presence of 1 µg of control autoantibodies anti C1 or C2). Each reaction mixture was incubated twice with protein A sepharose beads to eliminate antibodies.

Each reaction mixture was then coated in duplicate to ELISA plates and blocked with PBS containing 5% milk. To detect citrullination of fibrinogen, a serum was used that contained autoantibodies to citrullinated fibrinogen but no autoantibodies to PAD4. After washing with 0.1% Tween 20, peroxydase conjugated anti-human IgG (Sigma, France) was added. Optical density (OD) was read at 405 nm. Activation or inhibition of citrullination by PAD4 was determined by measuring the ratio of the OD measured for the test sample and OD measured for the positive control. A ratio >1 indicated activation, a ratio <1 indicated inhibition.

Synthetic Peptides

Peptides (Neosystem, Strasbourg, France) were synthesized using a solid phase system and purified. A total of 65 20-mer peptides overlapping on 10 amino acids derived from PAD4 (locus NM_012387), residues 1 to 663.

Mapping of Peptides in PAD4

Plates were coated overnight with 10 μg/well of PAD4 peptides diluted in phosphate buffer saline (PBS), pH 7.4. Plates were blocked with PBS containing 5% milk. Sera diluted to 1:100 in PBS were incubated for 2 hours. After washing with 0.1% Tween 20, peroxydase-conjugated anti-human IgG (Sigma, France) was added. Optical density was read at 405 nm. Background OD was obtained by adding each serum to a well without peptides. Positive sera were defined as an OD value more than twice the background OD (I Auger et al., Ann. Rheum. Dis., 2007, 66: 1588-1593).

Statistical Analysis

P-values were calculated using the Chi square test.

Results

Inhibition of the Citrullination of Fibrinogen by Autoantibodies to PAD4

To test whether autoantibodies directed to PAD4 interfere with the activity of PAD4, fibrinogen citrullination was analyzed in presence of anti-PAD4 autoantibodies purified from 29 patients and 2 healthy controls. Detection of citrullination was then quantified by ELISA.

Inhibition of fibrinogen citrullination was observed for 22 out of 31 purified autoantibodies to PAD4; activation of fibrinogen citrullination was observed for 6 out of 31 purified autoantibodies to PAD4; and 3 out of 31 purified autoantibodies to PAD4 were found to have no effect on fibrinogen citrullination (FIG. 1).

Four Linear Epitopes in PAD4 are Recognized by Autoantibodies to PAD4

To identify B cell epitopes in PAD4, 65 overlapping 20-mer peptides encompassing the entire sequence of human PAD4 were synthesized. These peptides were screened with the sera of 29 RA patients and 2 controls known to contain anti-PAD4 autoantibodies.

Among the 65 peptides, 18 peptides were recognized by the sera tested. Ten (10) of these peptides are located in the N terminal domain and the other 8 peptides are located in the C terminal domain. Four (4) peptides (22, 28, 61 and 63) were preferentially recognized by the sera of RA patients and controls (Table 1). Indeed, 15 out of 31 sera from RA patients were positive for peptide 22, 25 out of 31 were positive for peptide 28, 8 out of 31 were positive for peptide 61, and 16 out of 31 were positive for peptide 63. Peptides 22 and 28 are located in the N terminal domain of PAD4, while peptides 61 and 63 are located in the C terminal domain of PAD4.

Three Linear Epitopes in PAD4 are Associated with RA Patients

To confirm the reactivity observed, the sera of 33 patients with spondylarthropathy (AS) and 33 healthy individuals were tested by ELISA using peptides 22, 28, 61 and 63 as immunosorbents.

TABLE 1

Binding of PAD4 peptides to anti-PAD4 autoantibodies (in grey: positive peptide).

| | Subjects | PAD4 peptides N terminal | | | | | | | | | |
|---|---|---|---|---|---|---|---|---|---|---|---|
| | | 5 | 9 | 15 | 16 | 18 | 22 | 25 | 26 | 27 | 28 |
| I | RA1 | | | | | | | | | | |
| | RA2 | | | | | | ▓ | | | | |
| | RA3 | | | | | | | | | | ▓ |
| | RA4 | | | | ▓ | | ▓ | | | | ▓ |
| | RA5 | | | | | | ▓ | | | | |
| | RA6 | | | | | | ▓ | | | | ▓ |
| | RA7 | | | | | | ▓ | | | | ▓ |
| | RA8 | | | | | | | | | | ▓ |
| | RA9 | | | | | | | | | | ▓ |
| | RA10 | | | | | | | | | | ▓ |
| | RA11 | | | | | | ▓ | | | | ▓ |
| | RA12 | | | | | | ▓ | | | | ▓ |
| | RA13 | | | | | | ▓ | | | | ▓ |
| | RA14 | | | | | | | | | | ▓ |
| | RA15 | | | | | | ▓ | | ▓ | | ▓ |
| | RA16 | | | | | | ▓ | ▓ | | | ▓ |
| | RA17 | | ▓ | ▓ | | | | | | ▓ | ▓ |

TABLE 1-continued

Binding of PAD4 peptides to anti-PAD4 autoantibodies (in grey: positive peptide).

| | Subject | | | | | | | |
|---|---|---|---|---|---|---|---|---|
| O | RA18 | | | | ▓ | | | ▓ |
| | RA19 | | | | | | | ▓ |
| | RA20 | ▓ | ▓ | | ▓ | | ▓ | ▓ |
| | RA21 | | | | | | | ▓ |
| | RA22 | | | | ▓ | | | ▓ |
| | RA23 | | | | | | | ▓ |
| A | RA24 | | | | | | | ▓ |
| | RA25 | | | | | | | ▓ |
| | RA26 | | | ▓ | ▓ | | | ▓ |
| | RA27 | | | | | | | |
| | RA28 | | | | ▓ | | | ▓ |
| | RA29 | | | | | | | |
| I | CTL1 | | | | | | | ▓ |
| | CTL2 | | | | | | | |

| | | PAD4 peptides C terminal | | | | | | | |
|---|---|---|---|---|---|---|---|---|---|
| | Subjects | 33 | 49 | 51 | 59 | 61 | 62 | 63 | 64 |
| I | RA1 | | | | | | ▓ | | |
| | RA2 | | | | | ▓ | | | |
| | RA3 | | | | | | | | |
| | RA4 | | | | | ▓ | ▓ | ▓ | |
| | RA5 | | | | | ▓ | | | |
| | RA6 | ▓ | | | | | | | |
| | RA7 | | | | | | | | |
| | RA8 | | | | | ▓ | ▓ | ▓ | ▓ |
| | RA9 | | | | | | | | |
| | RA10 | | | | | | | ▓ | |
| | RA11 | ▓ | | | | | | ▓ | |
| | RA12 | | | | | | | ▓ | |
| | RA13 | | | | | | | ▓ | |
| | RA14 | | | | | | | ▓ | |
| | RA15 | | | | | | | ▓ | |
| | RA16 | | | | | ▓ | | ▓ | |
| | RA17 | | | | | | | | |
| | RA18 | | | | ▓ | | | | |
| | RA19 | | | | | | | | |
| | RA20 | | | ▓ | | ▓ | ▓ | ▓ | |
| O | RA21 | | | | | ▓ | ▓ | ▓ | ▓ |
| | RA22 | ▓ | ▓ | | | ▓ | ▓ | ▓ | |
| | RA23 | | | | | | | | ▓ |
| A | RA24 | | | | | | | ▓ | |
| | RA25 | | | | | | | ▓ | |
| | RA26 | | | | | | | | |
| | RA27 | | | | | | | | |
| | RA28 | | | | | | | ▓ | |
| | RA29 | | | | | | | | |

TABLE 1-continued

Binding of PAD4 peptides to anti-PAD4 autoantibodies (in grey: positive peptide).

| I | CTL1 | ▒ |
| | CTL2 | |

I = Inhibition of fibrinogen citrullination by PAD4;
0 = no effect on fibrinogen citrullination by PAD4;
A = activation of fibrinogen citrullination by PAD4

Figure 2:
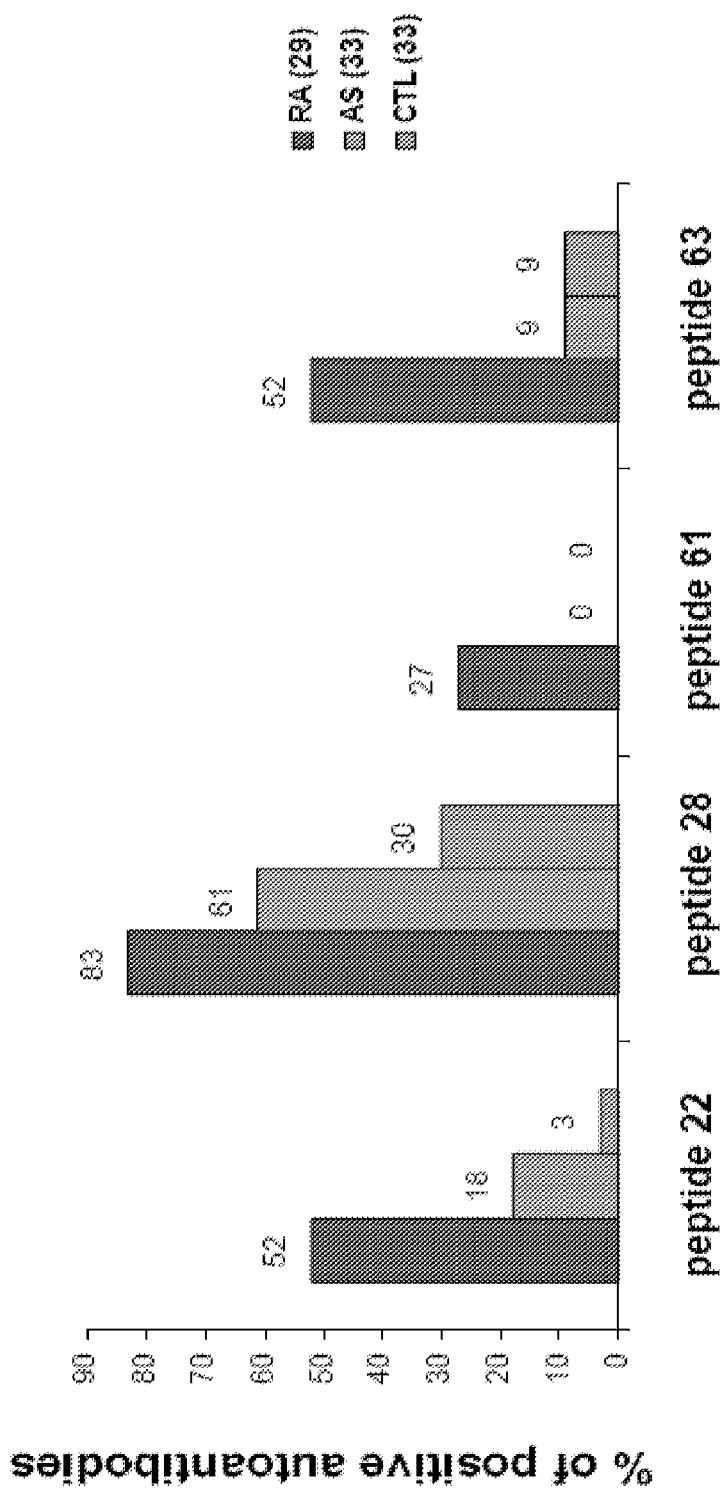
FIG. 2 is a graph showing, for each group of sera from RA patients, AS patients and healthy controls, the percentage of sera that recognize peptide 22, peptide 28, peptide 61 and peptide 63. Positive sera were defined as sera for which an OD value of more than twice the background was measured (see Examples section for experimental details).

Autoantibodies against peptide 22, peptide 61 and peptide 63 were found in more RA patients than controls (FIG. 2). Indeed, 15 of 29 RA patients were positive for peptide 22 versus 7 out of 66 controls (p=0 by Chi square test). Similarly, 8 out of 29 RA patients were positive for peptide 61 versus none out of 66 controls (p=0 by chi square test). Finally, 15 out of 29 patients were positive for peptide 63 versus 6 out of 66 controls (p=0 by Chi square test).

Autoantibodies against peptide 28 were found in high percentage in controls. Indeed, 24 of 29 patients were positive versus 20 out of 33 AS patients and 10 out of 33 healthy individuals (p=0.002 by Chi square test, 29 patients versus 66 controls).

Peptide Recognition by Autoantibodies to PAD4 and Inhibition of Citrullination by PAD4

The peptide pattern of autoantibodies to PAD4 that inhibit (patients RA1 to RA20), that activate (patients RA24 to RA29), or that have no effect (patients RA21 to RA23) on citrullination by PAD4 was analyzed.

Figure 3:
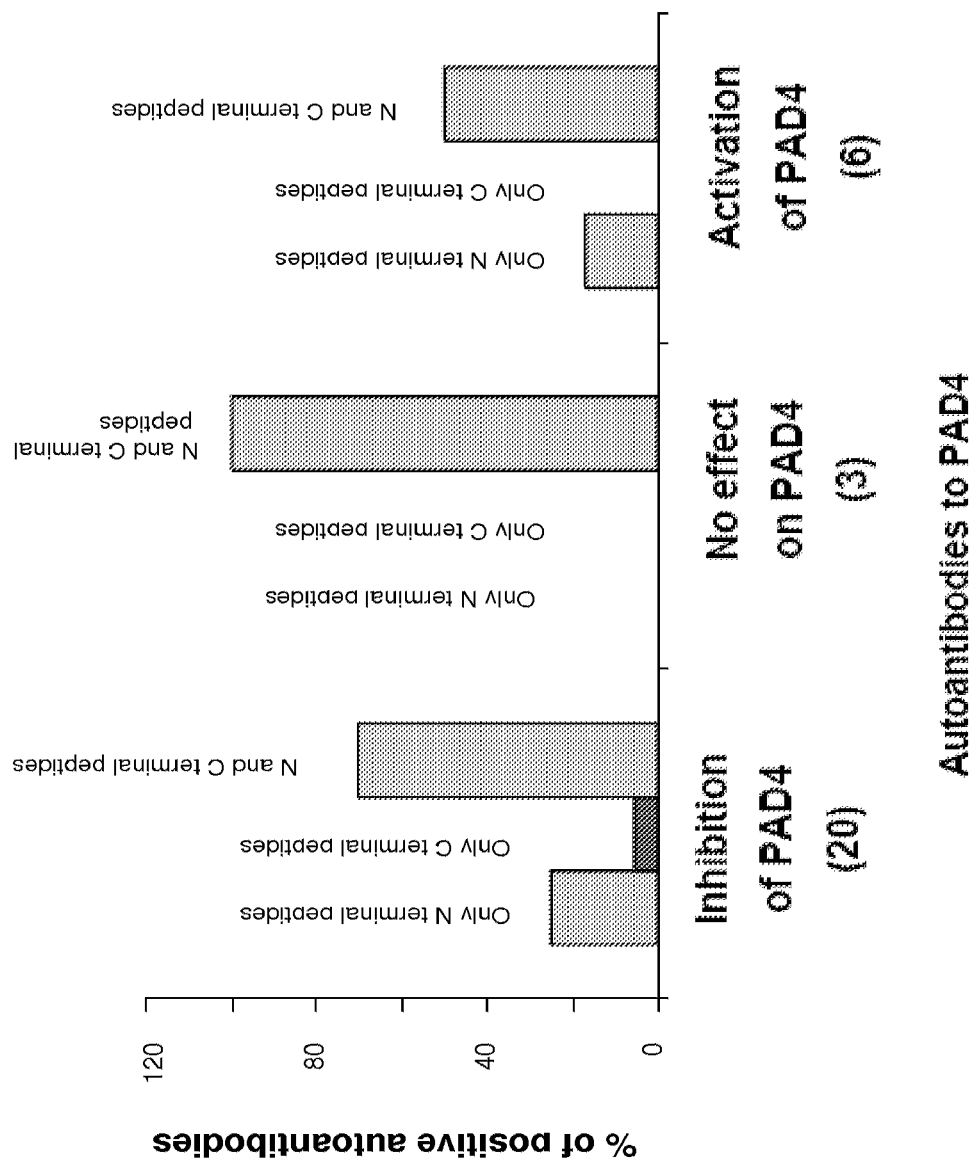
FIG. 3 is a graph showing, for each group of anti-PAD4 autoantibodies that inhibit citrullination of fibrinogen (patients RA1 to RA20), that activate citrullination of fibrinogen (patients RA24 to RA29) and that have no effect on citrullination of fibrinogen (patients RA21 to RA23), the percentage of autoantibodies that recognize N terminal peptides only, C terminal peptides only, or both N terminal peptides and C terminal peptides.

No difference was observed in the number of peptides recognized by autoantibodies known to inhibit or activate PAD4 (Table 2). Irrespective of their action (activation or inhibition), most autoantibodies to PAD4 recognized peptides located in the N terminal domain and the C terminal domain. Among autoantibodies to PAD4 that inhibit PAD4, 5 out of 20 recognized exclusively peptides located in the N terminal domain, 1 out of 20 recognized exclusively peptides located in the C terminal domain and 14 out of 20 recognized peptides located in the N terminal domain and the C terminal domain (FIG. 3).

Among autoantibodies to PAD4 that have no effect on citrullination by PAD4, 3 out of 3 recognized peptides located in the N terminal domain and the C terminal domain.

Among autoantibodies to PAD4 that activate PAD4, 1 out of 6 recognized exclusively peptides located in the N terminal domain, none of out of 6 recognized peptides located in the C terminal domain and 3 out of 6 recognized peptides located in the N terminal domain and the C terminal domain.

Figure 4:
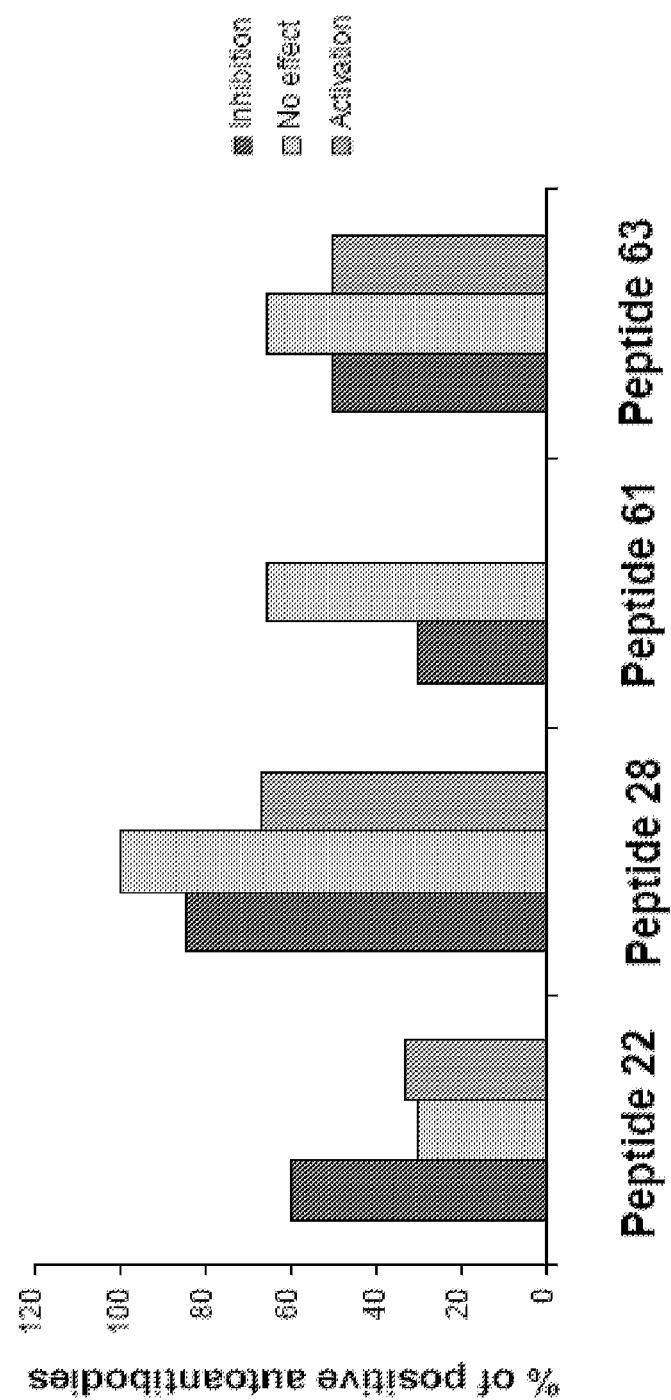
FIG. 4 is a graph showing, for each group of autoantibodies to PAD4 that recognize peptide 22, peptide 28, peptide 61 and peptide 63, the percentage of autoantibodies that inhibit, activate or have no effect on citrullination of fibrinogen.

Peptides 22 and 61 were preferentially recognized by autoantibodies to PAD4 that inhibit PAD4 (FIG. 4). Indeed, 12 out of 20 autoantibodies to PAD4 that inhibit PAD4 were positive to peptide 22 compared to 2 out of 6 autoantibodies to PAD4 that activated PAD4. Moreover, peptide 61 was recognized by 6 out of 20 autoantibodies to PAD4 that inhibit PAD4 versus none of 6 autoantibodies to PAD4 that activate PAD4. However, among autoantibodies to PAD4 found to have no effect on citrullination of PAD4, 2 out of 3 recognized peptide 61.

Discussion

Using protein arrays and ELISA assays, the present applicants have previously found that PAD4 is a specific autoantigen in RA patients. Autoantibodies against PAD4 have already been described in RA. PAD4 is involved in the generation of citrullinated epitopes. Autoantibodies to citrullinated epitopes are highly specific of RA. The presence of these autoantibodies before the onset of RA suggests a potential role in the pathophysiology of the disease.

The study presented herein was undertaken to test whether autoantibodies to PAD4 interfere with the activity of PAD4. The applicants have developed an in house citrullination assay with PAD4, fibrinogen and autoantibodies to PAD4 purified from the sera of RA patients. As a general rule, it was observed that autoantibodies to PAD4 inhibit the citrullination of fibrinogen by PAD4. Indeed, 22 out of 31 purified autoantibodies to PAD4 were found to inhibit fibrinogen citrullination by PAD4.

In order to identify the epitopes recognized by autoantibodies to PAD4, 65 20-mer peptides encompassing the entire sequence of PAD4 were used in a direct ELISA assay. Autoantibodies to PAD4 were found to recognize four major epitopes: peptide 22 (corresponding to amino acid residues 211-230 of human PAD4); peptide 28 (amino acid residues 271-290); peptide 61 (amino acid residues 601-620) and peptide 63 (amino acid residues 621-640). Peptides 22 and 28 are located in the N terminal domain of PAD4 (which encompasses amino acid residues 1 to 300), while peptides 61 and 63 are located in the C terminal domain of PAD4 (which encompasses amino acid residues 301 to 663). Autoantibodies that recognize peptides 22, 61 and 63 were found in high percentage in RA patients compared to controls.

Five $Ca^{2+}$-binding motifs have been identified in PAD4, three are in the N terminal domain and two are in the C terminal domain (K Arita et al., Proc. Natl. Acad. Sci. USA, 2006, 10: 5291-5296; K Arita et al., Natl. Struct. Mol. Biol., 2004, 11: 777-783). The N terminal domain seems to be involved in conformational changes mediated by $Ca^{2+}$. After binding to $Ca^{2+}$, conformational changes generated an active cleft and substrate binds PAD4. The N terminal domain may also influence the enzymatic activity of PAD4. Indeed, the PADI4 gene presents two major haplotypes. In some populations, one is RA-susceptible and the other is not RA-susceptible. These two haplotypes contain four single nucleotide polymorphisms (SNPs) in exons of the N terminal domain (position 55, 82, 112 and 117). The C terminal domain contains the substrate binding domain and the catalytic domain.

In 2008, Harris et al. mapped epitopes in PAD4 by immunoprecipitation of in vitro-translated PAD4 truncations with autoantibodies to PAD4 (M. L. Harris et al., Arthritis Rheum., 2008, 58(7): 1958-1967). Two types of sera were identified. Type I sera were found to recognize exclusively full length PAD4 (1-663) and type II sera were found to recognize both full-length (1-663) and truncated PAD4 (1-523). Type II autoantibodies to PAD4 require exclusively contributions from the N terminal domain of PAD4 (1-119). However, type I autoantibodies to PAD4 require contributions from the N terminal domain (1-119) and the C terminal domain (523-663) of PAD4.

In the protein arrays and ELISA assays performed by the present Applicants, every autoantibody to PAD4 recognized the full-length PAD4 (1-663) (I Auger et al., Ann. Rheum. Dis., 2008 Oct. 28). Among autoantibodies to PAD4 from RA patients, only 3 out of 29 recognized the truncated PAD4 (residues 1 to 111) (data not shown). In the extensive peptide assay, 7 out of 29 autoantibodies to PAD4 recognized exclusively the peptides located in the N terminal domain (211-290) of PAD4. One out of 29 autoantibodies to PAD4 recognized exclusively the peptide located in the C terminal domain (611-630). Finally, 19 out of 29 autoantibodies to PAD4 were found to recognize the peptides located in the N terminal domain (211-290) and the C terminal domain (601-650).

Figure 5:
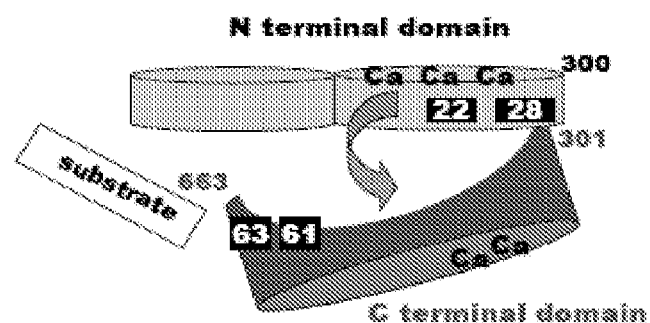
FIG. 5 is a scheme presenting a model that explains how autoantibodies to PAD4 could inhibit PAD4. (A) Calcium binding could open the substrate binding domain of PAD4. (B) The substrate could then bind to PAD4 and be citrullinated. (C) Autoantibodies to PAD4 may interfere with conformation change or substrate binding.
Figure 5:
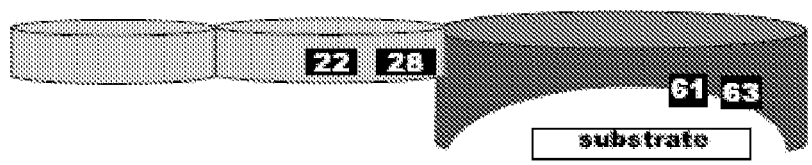
Figure 5:
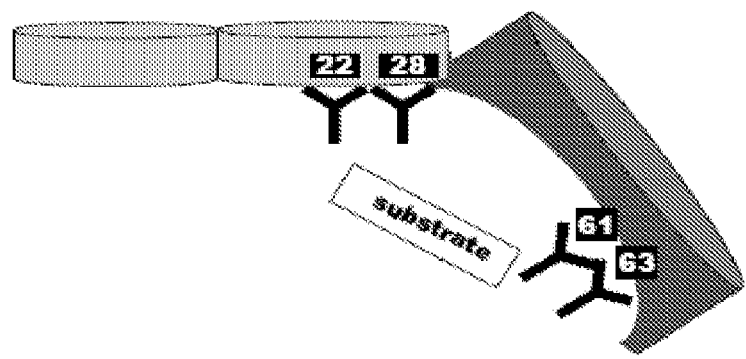

The majority of autoantibodies to PAD4 were found to inhibit the citrullination of fibrinogen by PAD4. Most autoantibodies recognize peptides located in the N terminal domain (mostly peptide 22 or peptide 28) and the C terminal domain (mostly peptide 61 or peptide 63). Without wishing to be bound by theory, the applicants propose the following model to explain how autoantibodies to PAD4 inhibit citrullination (FIG. 5): interaction of autoantibodies with peptide 22 or peptide 28 may interfere with conformational changes mediated by $Ca^{2+}$ binding. Calcium binding and substrate binding are important to generate the active site in PAD4 (K Arita et al., Nat. Struct. Mol. Biol., 2004, 11: 777-783). It is also possible that because autoantibodies to PAD4 bind to 40 amino acids within the C terminal domain of PAD4, the interaction of PAD4 with its substrate is blocked. This may explain why autoantibodies to PAD4 inhibit citrullination mediated by PAD4.

It still remains to elucidate how this inhibition may influence the development of anti-citrullin immunization in RA patients. The applicants are in the process of studying this question.

Example II

BRAF-Peptides for RA Diagnosis in CCP-Negative

Patients and Methods
RA Patients and Controls

118 RA patients were selected from the Rheumatology Ward at Hospital La Conception, Marseille, France. These patients fulfilled the 1987 American College of Rheumatology criteria for RA. For all patients, HLA-DR genotyping and anti CCP titration were obtained. 89 of the 118 RA patients were CCP positive and 29 RA patients were CCP negative. Patients (33) with spondylarthropathy (AS) from the same hospital in Marseille and healthy volunteers (60) from the staff of INSERM UMR639 and of Marseille Blood Transfusion Center) were used as controls.

Synthetic Peptides

Forty 20-mer peptides encompassing residues 416 to 766 from BRAF (locus NP_004324.1) were synthesized using a solid phase system and purified (Neosystem, Strasbourg, France). BRAF sequence used for peptide synthesis displayed polymorphism at position 599 (V599E, valine replaced with glutamate), a mutation observed in human cancers and associated with increased kinase activity.

Detection of Autoantibodies by ELISA

Plates were coated overnight with 10 μg/well of peptide diluted in phosphate buffer saline (PBS), pH7.4. Plates were blocked with PBS containing 5% milk. Sera diluted to 1:100 in PBS were incubated for 2 hours. After washing with 0.1% Tween 20, peroxydase conjugated anti human IgG, (Sigma, France) was added. Optical density (OD) was read at 405 nm. Background OD was obtained by adding each serum to a well in the absence of protein. A positive serum was defined as one presenting an OD value more than twice the background OD.

Statistical Analysis

The p-values were calculated using the Chi squareTest.

Results
Autoantibodies to BRAF Recognize 4 Linear Epitopes in BRAF

To identify B cell epitopes on BRAF, 40 20-mer peptides encompassing the catalytic domain of BRAF were synthesized. These 40 peptides were screened with the sera of 21 RA patients known to contain autoantibodies to BRAF. Among the 40 peptides, 14 were recognized by the tested sera. Four peptides, P10 (SEQ ID NO: 7, positions 506-525 of human BRAF,), P16 (SEQ ID NO: 8, positions 566-585 of human BRAF,), P25 (SEQ ID NO: 9, positions 656-675 of human BRAF), and P33 (SEQ ID NO: 13) were preferentially recognized by the sera of RA patients. Indeed, 18 of 21 sera recognized P10, 8 recognized P16, 15 recognized P25, and 6 recognized P33 (see Table 2).

Three Linear Epitopes on BRAF are Recognized by RA Patients

Figure 6:
FIG. 6 is a graph showing the binding of BRAF-peptides to autoantibodies to BRAF. BRAF-peptides, P10, P16, P25 and P33 were tested by ELISA in the sera of 21 RA patients, 33 SPA patients, and 60 healthy volunteers. After washing, peroxydase conjugated anti human IgG was added, and optical density was read at 405 nm. Background OD was obtained by adding each serum to a well without peptide. Positive sera were defined by OD value higher than twice background OD.
Figure 8:
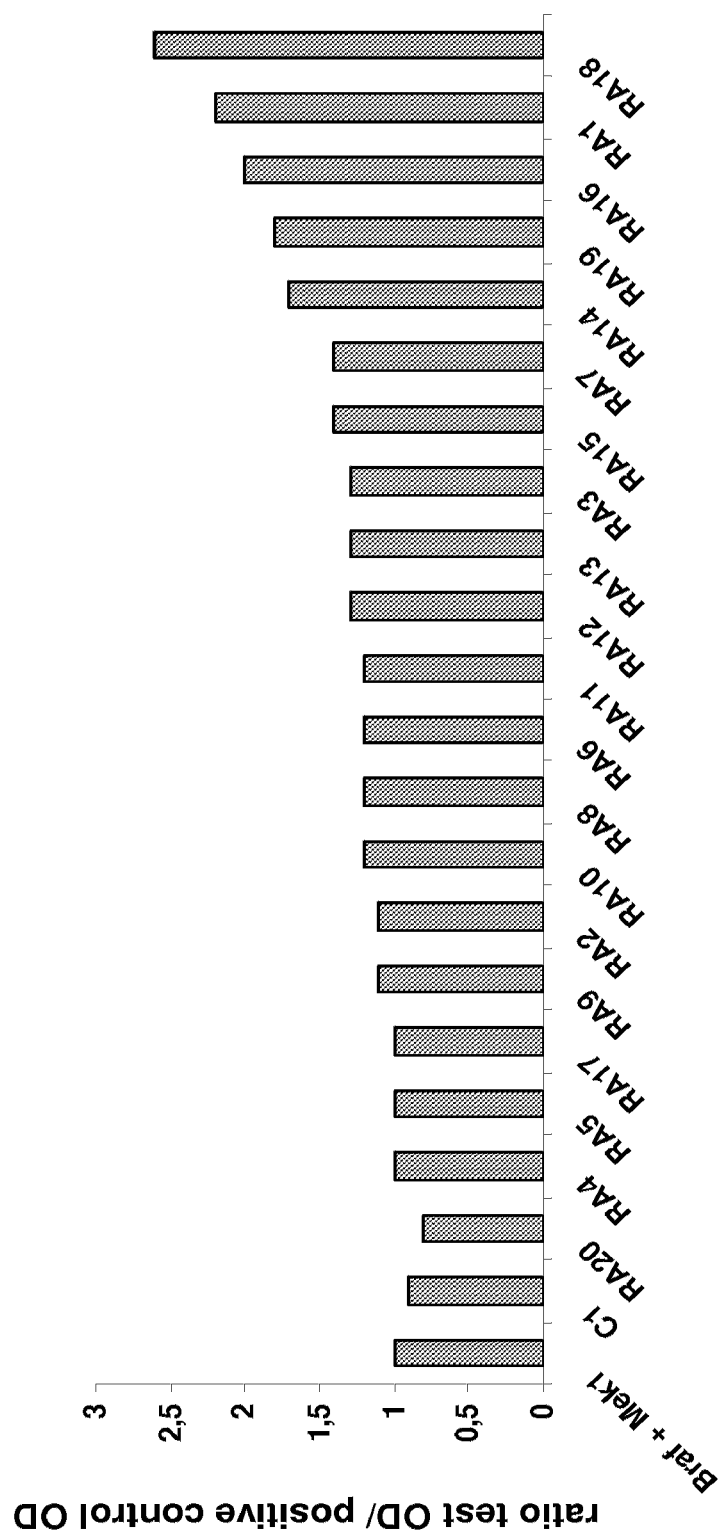
FIG. 8 is a graph showing that autoantibodies to BRAF present in the serum of RA patients activate the phosphorylation of MEK1. Purified anti-BRAF autoantibodies from patients were incubated with BRAF and MEK1. For each patient, one positive control (BRAF and MEK1) and one negative control (BRAF and MEK1 and C1 control antibody) were included. Activation or inhibition of MEK1 phosphorylation was detected by measuring the ratio test OD/positive control OD. Ratio >1 indicated activation, ratio <1 indicated inhibition.

To confirm the reactivity observed, we tested by ELISA the sera of 33 patients with spondylarthropathy (AS) and of 60 healthy individuals were tested by ELISA in the presence of P10, P16, P25 and P33. Autoantibodies to P10, P16, and P25 were found in RA patients more often than in controls (see FIG. 6). Indeed, 18 of 21 patients sera recognized P10 versus 10 of 93 controls ($p<10^{-7}$ by Chi square test). Similarly, 8 of 21 RA patients sera recognized P16 versus 1/93 controls ($p<10^{-7}$ by Chi square test). Finally, 15 of 21 RA patients sera recognized P25 versus 0/93 controls ($p<10^{-7}$ by Chi square test). Antibodies to P33 were less specific for RA. 6 of 21 RA patients, but also 6/33 AS patients and 13/60 healthy individuals had anti P33 antibodies (p=0.523 by Chi square test, 21 RA patients versus 93 controls).

TABLE 2

Binding of BRAF peptides to anti-BRAF autoantibodies (in grey: positive peptide).

| | RA patients | | | | | | | | | | |
|---|---|---|---|---|---|---|---|---|---|---|---|
| | 1 | 2 | 3 | 4 | 5 | 6 | 7 | 8 | 9 | 10 | 11 |
| P1 | | | | | | | | | | | |
| P2 | | | | | | | | | | | |
| P3 | | | | | | | | | | | |
| P4 | | | | | | | | | | | |
| P5 | | | | | | | | | | | ▓ |
| P6 | | | ▓ | | | ▓ | | | | | |
| P7 | | | | | | | | | | | |
| P8 | | | | | | | | | | | |
| P9 | | | | | | | | | | | |
| P10 | ▓ | | ▓ | ▓ | ▓ | ▓ | ▓ | ▓ | ▓ | ▓ | ▓ |

TABLE 2-continued

Binding of BRAF peptides to anti-BRAF autoantibodies (in grey: positive peptide).

| | 2 | 3 | 4 | 5 | 6 | 7 | 8 | 9 | 10 | 11 |
|---|---|---|---|---|---|---|---|---|---|---|
| P11 | | | | | | | ▓ | ▓ | ▓ | |
| P12 | | | | | | | | | | |
| P13 | | | | | | | | | | |
| P14 | | | | | | | | | | |
| P15 | | | | | | | | | | |
| P16 | | | ▓ | | ▓ | | | | | ▓ |
| P17 | | | | | | | | | | |
| P18 | | | | | | | | | | |
| P19 | | | | | | | | | | |
| P20 | | | | | | | | | | |
| P21 | | | | | | | | | | |
| P22 | | | | | | | | | | |
| P23 | | | | | | | | | | |
| P24 | | | | | | | | | | |
| P25 | | | | ▓ | ▓ | ▓ | ▓ | ▓ | ▓ | ▓ |
| P26 | | | | | | | | ▓ | ▓ | |
| P27 | | | | | | | | | | |
| P28 | | ▓ | | | | | | | ▓ | |
| P29 | | | | | | | | | | |
| P30 | | | | | | | | | | |
| P31 | | | | | | | | | | |
| P32 | | | | | | | | | | |
| P33 | ▓ | | | | ▓ | | | | ▓ | |
| P34 | | | | | | | | | | |
| P35 | | | | | | | | ▓ | ▓ | |
| P36 | | | | | | | | | | |
| P37 | | | | ▓ | | | | | ▓ | |
| P38 | | | | | | | | | | |
| P39 | | | | | | | | | | ▓ |
| P40 | | | | | | | | | | |

| | RA patients | | | | | | | | | |
|---|---|---|---|---|---|---|---|---|---|---|
| | 12 | 13 | 14 | 15 | 16 | 17 | 18 | 19 | 20 | 21 |
| P1 | | | | | | | | | | |
| P2 | | | | | | | | | | |
| P3 | | | | | | | | | | |
| P4 | | | | | | | | | | |
| P5 | | | | | | | | | | |
| P6 | | | | | | | | | | |
| P7 | | | | | | | | | | |
| P8 | | | | | | | | | | |
| P9 | | | | | | | | | | |
| P10 | ▓ | | | ▓ | ▓ | ▓ | ▓ | ▓ | ▓ | ▓ |
| P11 | | | | | | | | | | |
| P12 | | | | | | | | | | |
| P13 | ▓ | | | | | | | | | |
| P14 | | | | | | | | | | |
| P15 | | | | | | | | | | |
| P16 | ▓ | | | | | | ▓ | ▓ | ▓ | ▓ |
| P17 | | | | | | | | | | |
| P18 | | | | | | | | | | |
| P19 | | | | | | | | | | |
| P20 | | | | | | | | | | |
| P21 | | | | | | | | | | |
| P22 | | | | | | | | | | |
| P23 | | | | | | | | | | |
| P24 | | | | | | | | | | |
| P25 | | ▓ | ▓ | ▓ | | ▓ | ▓ | ▓ | ▓ | ▓ |
| P26 | | | | | | | | | | |
| P27 | | | | | | | | | | |
| P28 | | | | | | | | | | |
| P29 | | | | | | | | | | |
| P30 | | | | | | | | | | |

TABLE 2-continued

Binding of BRAF peptides to anti-BRAF autoantibodies (in grey: positive peptide).

| Peptide | | | | | | |
|---|---|---|---|---|---|---|
| P31 | ▓ | | | | | |
| P32 | | | | | | |
| P33 | | | ▓ | ▓ | ▓ | |
| P34 | | | | | | |
| P35 | | | | | | ▓ |
| P36 | | | | | | |
| P37 | | | | | | |
| P38 | | | | | | |
| P39 | | | ▓ | | ▓ | ▓ |
| P40 | | | | | | |

P10, P16 and P25 Peptides Identify RA in 50% of CCP-Negative Patients

The frequency of positive sera in CCP positive and CCP negative patients was calculated by ELISA using P10, P16 and P25 peptides as immunosorbent. Among CCP positive patients, 29/89 recognized P10, 7/89 recognized P16, and 17/89 recognized P25. Among CCP negative patients, 13/29 recognized P10, 1/29 recognized P16, and 8/29 recognized P25. In combination, P10, P16 and P25 identify 50% of CCP-negative patients (FIG. 7).

Conclusions

Three linear peptides on BRAF recognized almost uniquely by RA patients have been identified. P10 (SEQ ID NO: 7), P16 (SEQ ID NO: 8) and P25 (SEQ ID NO: 9) peptides are located in the catalytic domain of BRAF. These peptides were also recognized by the sera of CCP-negative patients. The combination of P10, P16 and P25 of BRAF identifies 50% of CCP-negative patients.

Example III

Biomarkers for RA Diagnosis in CCP-Negative Patients

Patients and Methods

RA Patients and Controls

More than a hundred (118) RA patients are selected from the Rheumatology Ward at Hospital La Conception, Marseille, France, as described above. One hundred controls (Patients with spondylarthropathy (AS) from the Rheumatology Ward at Hospital La Conception, Marseille and volunteers from the staffs of INSERM UMR639 and Marseille Blood Transfusion Center) were also tested.

Synthetic Peptides

Sixty five 20-mer peptides encompassing residues 1 to 663 from wild type PAD4 (NM_012387), 40 20-mer peptides encompassing residues 416 to 766 from BRAF (NP_004324.1) were synthesized using the solid phase system and purified (Neosystem, Strasbourg, France). Ninety-four 15-amino-acid peptides derived from calpastatin isoform A (locus NP_001035908), residues 1-708 were used.

In particular, PAD4 peptides: 22 (SEQ ID NO: 2), 61 (SEQ ID NO: 3) and 63 (SEQ ID NO: 4) are 20-mer peptides from locus NM_012387. BRAF peptides P10 (SEQ ID NO: 7), P16 (SEQ ID NO: 8) and P25 (SEQ ID NO: 9) are 20-mer peptides from locus NP_004324.1. Calpastatin peptides P'16 (SEQ ID NO: 11) and P'28 (SEQ ID NO: 12) are 15-mer peptides from locus NP_001741.

Detection of Autoantibodies by ELISA

The procedure used is identical to that descried in Example II.

Statistical Analysis

The p-values were calculated using the Chi squareTest.

Results

Eight Peptides (3 PAD4-Peptides, 3 BRAF-Peptides and 2 Calpastatin-Peptides) are Recognized by RA Patients.

Figure 9:
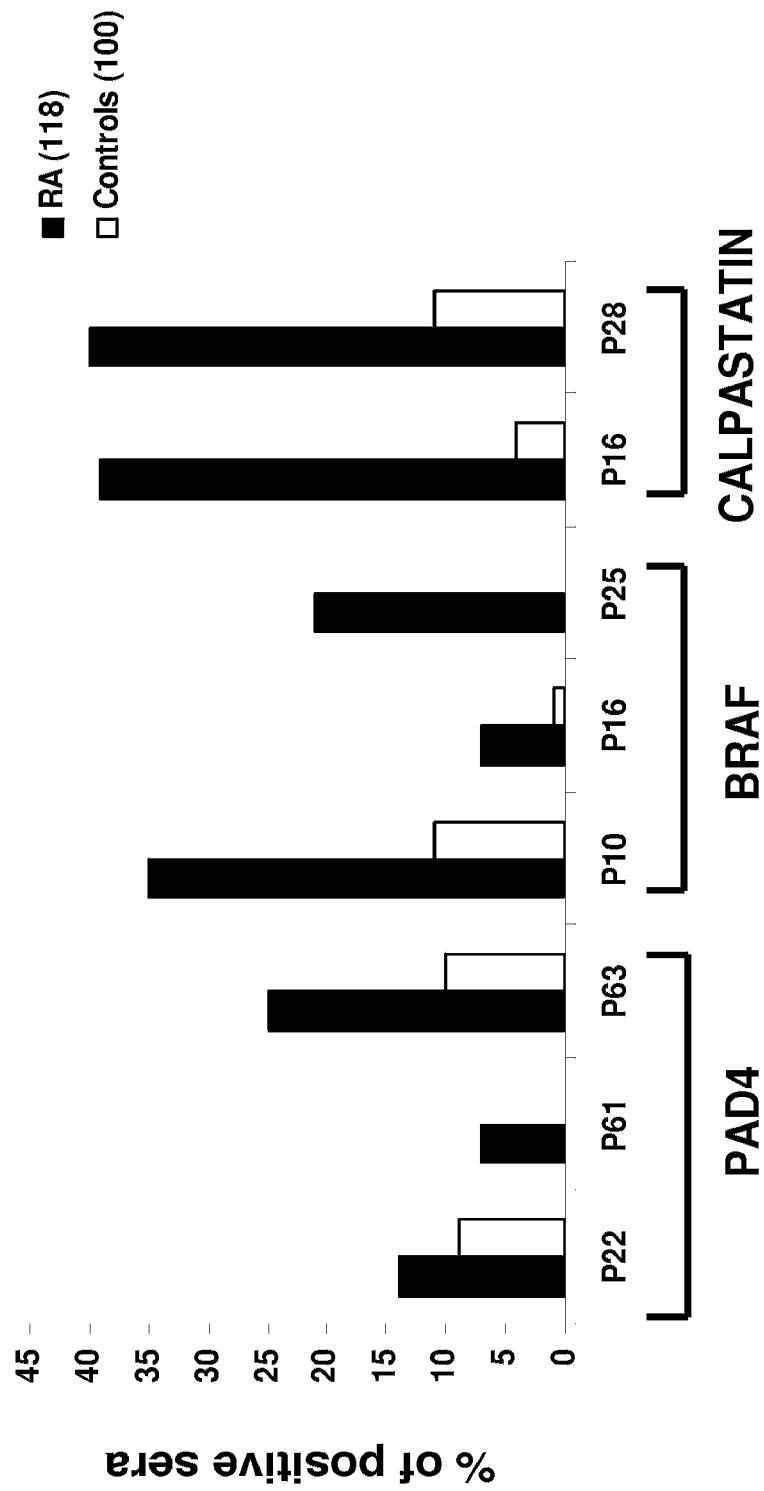
FIG. 9 is a graph showing the binding of PAD4-, BRAF- and Calpastatin-peptides to autoantibodies present in the serum of RA patients. PAD4-peptides (peptides 22, 61 and 63), BRAF-peptides (P10, P16 and P25) and Calpastatin-peptides (P'16 and P'28) were contacted with the sera of 118 RA patients and of 100 control sera. Binding was determined and assessed as described in Example II.

The Applicants have identified three linear peptides on PAD4 that are preferentially recognized by sera from patients with RA: peptides 22, 61 and 63; three linear peptides on BRAF that are recognized almost solely by RA patients: P10, P16, P25; and two linear peptides on calpastatin that are preferentially associated with RA patients: P'16 and P'28 (see FIG. 9).

The Eight Peptides are Recognized by CCP-Negative Patients

Figure 10:
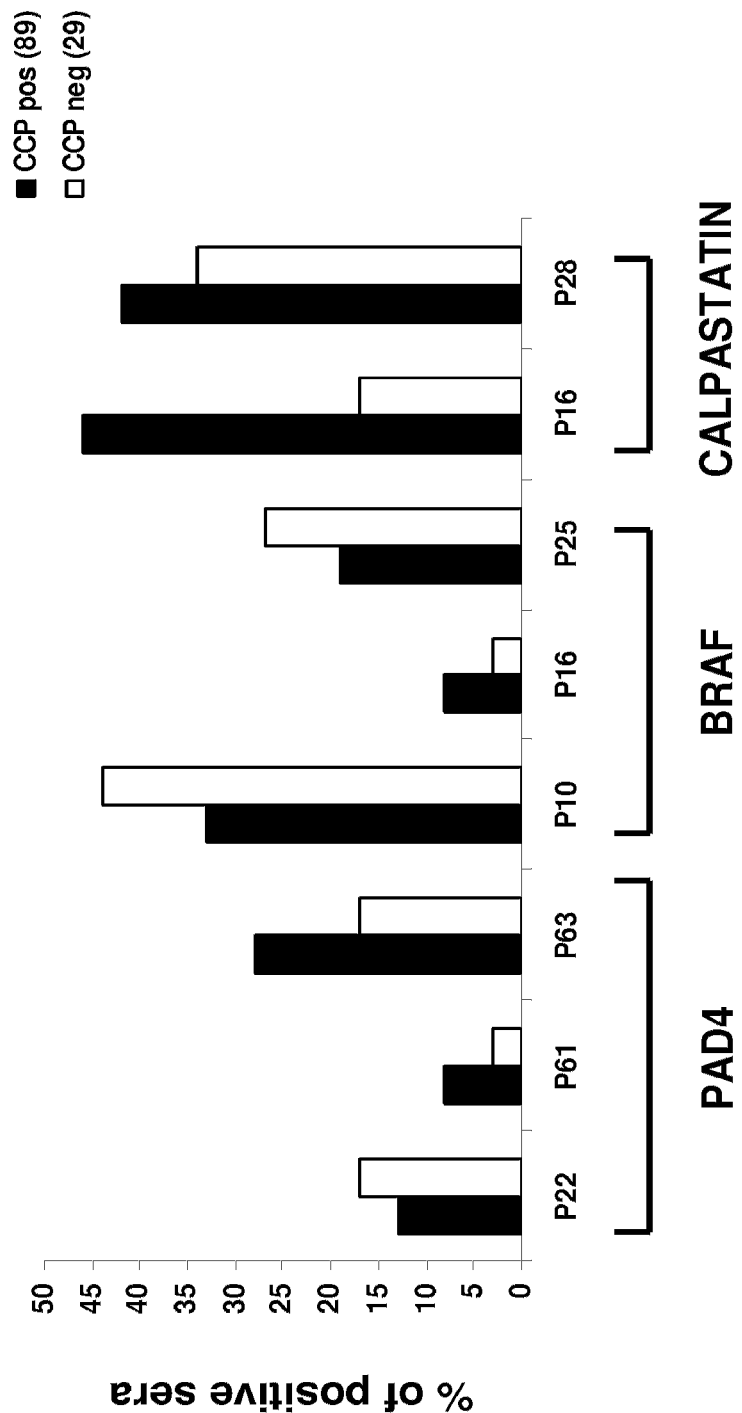
FIG. 10 is a graph showing that PAD4-peptides (peptides 22, 61 and 63), BRAF-peptides (P10, P16 and P25) and Calpastatin-peptides (P'16 and P'28) are recognized by CCP-negative patients. These peptides were contacted with the sera of 83 CCP-negative RA patients and 29 CCP-negative RA patients. Binding was determined and assessed as described in Example II.

These 8 peptides were recognized by the sera of CCP-negative patients (see FIG. 10). The most efficient binders are P10 of BRAF and P'28 of calpastatin. P10 of BRAF is recognized by 44% of CCP-negative patients and P'28 of calpastatin by 34% of CCP-negative patients.

Combination of PAD4-, BRAF- and Calpastatin-Peptides Recognizes RA in 72% of CCP-Negative Patients For one autoantigen, the best combination to identify CCP-negative patients is BRAF peptides. The combination of P10, P16 and P25 of BRAF identifies 50% of CCP-negative patients. For two autoantigens, the combination of BRAF peptides and calpastatin peptides identifies 69% of CCP-negative patients. Finally, the combination of PAD4-, BRAF- and calpastatin-peptides identifies 72% of CCP-negative patients.

Conclusions

The present Applicants have found 8 peptides (3 peptides of PAD4, 3 peptides of BRAF and 2 peptides of calpastatin) allowing the identification of 72% of CCP-negative patients.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

The invention claimed is:

1. A kit for detecting the presence of anti-PAD4 autoantibodies or anti-BRAF autoantibodies in a biological sample, said kit comprising:
   at least one biomarker,
   wherein the at least one biomarker is a PAD4-peptide (i) selected from the group consisting of SEQ ID NO: 2, SEQ ID NO: 3, SEQ ID NO: 4, and SEQ ID NO: 5, or (ii) consisting of a fragment of PAD4 of less than 50 amino acids and comprising a sequence selected from the group consisting of SEQ ID NO: 2, SEQ ID NO: 3, SEQ ID NO: 4, and SEQ ID NO: 5, or
   wherein the at least one biomarker is a BRAF-peptide (i) selected from the group consisting of SEQ ID NO: 7, SEQ ID NO: 8, and SEQ ID NO: 9, or (ii) consisting of a fragment of BRAF catalytic domain of less than 50 amino acids and comprising a sequence selected from the group consisting of SEQ ID NO: 7, SEQ ID NO: 8, and SEQ ID NO: 9; and
   at least one reagent for detecting a biomarker-antibody complex formed between the biomarker and an autoantibody present in the biological sample, wherein the autoantibody is an anti-PAD4 autoantibody or an anti-BRAF autoantibody that is indicative of rheumatoid arthritis, and wherein the at least one reagent is an anti-human IgG labelled with a detectable moiety.

2. The kit according to claim 1, wherein the detectable moiety is selected from enzymes, fluorophores, radioisotopes, chemiluminescent moieties and biochemiluminescent moieties.

3. The kit according to claim 2, wherein:
   the at least one biomarker is the PAD4-peptide selected from the group consisting of SEQ ID NO: 2, SEQ ID NO: 3, SEQ ID NO: 4, and SEQ ID NO: 5, or
   the at least one biomarker is the BRAF-peptide selected from the group consisting of SEQ ID NO: 7, SEQ ID NO: 8, and SEQ ID NO: 9.

4. The kit according to claim 3, wherein the detectable moiety is selected from enzymes, fluorophores, radioisotopes, chemiluminescent moieties and biochemiluminescent moieties.

5. The kit according to claim 1, wherein the fragment of PAD4 of less than 50 amino acids recognizes anti-PAD4 autoantibodies, and wherein the fragment of BRAF catalytic domain of less than 50 amino acids recognizes anti-BRAF autoantibodies.

* * * * *